(12) United States Patent
Becker et al.

(10) Patent No.: US 6,534,274 B2
(45) Date of Patent: *Mar. 18, 2003

(54) MOLECULAR TORCHES

(75) Inventors: Michael M. Becker, San Diego, CA (US); Gary P. Schroth, Foster City, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/001,344

(22) Filed: Oct. 31, 2001

(65) Prior Publication Data

US 2002/0090633 A1 Jul. 11, 2002

Related U.S. Application Data

(63) Continuation of application No. 09/346,551, filed on Jul. 1, 1999, now Pat. No. 6,361,945.
(60) Provisional application No. 60/091,616, filed on Jul. 2, 1998.

(51) Int. Cl.[7] .......................... C12Q 1/68; C07H 21/04
(52) U.S. Cl. ......................................... 435/6; 536/24.3
(58) Field of Search ............................. 435/6; 536/24.3

(56) References Cited

U.S. PATENT DOCUMENTS

| 4,766,062 A | 8/1988 | Diamond et al. |
| 4,820,630 A | 4/1989 | Taub |
| 4,822,733 A | 4/1989 | Morrison |

(List continued on next page.)

FOREIGN PATENT DOCUMENTS

| EP | 0070685 A2 | 1/1983 |
| EP | 0229943 A2 | 7/1987 |
| EP | 0601889 A2 | 6/1994 |
| WO | 9513399 A1 | 5/1995 |
| WO | 9723647 A1 | 7/1997 |
| WO | 9739008 A1 | 10/1997 |
| WO | 9802582 A2 | 1/1998 |
| WO | 9810096 A1 | 3/1998 |
| WO | 9922018 A2 | 5/1999 |

OTHER PUBLICATIONS

Bonnet et al., "Kinetics of Conformational Fluctuations in DNA Hairpin–Loops", Proc. Natl. Acad. Sci., Jul. 1998, pp. 8602–8606, vol. 95, No. 15, The National Academy of Sciences, US.

Cardullo et al., "Detection of nucleic acid hybridization by nonradiative fluorescence resonance energy transfer", Proc. Natl. Acad. Sci., Dec. 1988, pp. 8790–8794, vol. 85, No. 23, The National Academy of Sciences, US.

Giesendorf et al., "Molecular Beacons: A New Approach for Semiautomated Mutation Analysis", Clinical Chemistry, Mar. 1998, pp. 482–486, vol. 44, No. 3, American Association for Clinical Chemistry, Inc., US.

Holland et al., "Detection of specific polymerase chain reaction product by utilizing the 5'–3' exonuclease activity of Thermus aquaticus DNA polymerase", Proc. Natl. Acad. Sci, Aug. 1991, pp. 7276–7280, vol. 88, No. 16, The National Academy of Sciences, US.

(List continued on next page.)

Primary Examiner—Kenneth R. Horlick
(74) Attorney, Agent, or Firm—Charles B. Cappellari; Sheldon O. Heber

(57) ABSTRACT

The present invention features "molecular torches" and the use of molecular torches for detecting the presence of a target nucleic acid sequence. Molecular torches contain a target binding domain, a target closing domain, and a joining region. The target binding domain is biased towards the target sequence such that the target binding domain forms a more stable hybrid with the target sequence than with the target closing domain under the same hybridization conditions. The joining region facilitates the formation or maintenance of a closed torch.

65 Claims, 12 Drawing Sheets

U.S. PATENT DOCUMENTS

| | | | |
|---|---|---|---|
| 4,996,143 | A | 2/1991 | Heller et al. |
| 5,118,801 | A | 6/1992 | Lizardi et al. |
| 5,210,015 | A | 5/1993 | Gelfand et al. |
| 5,283,174 | A | 2/1994 | Arnold, Jr. et al. |
| 5,312,728 | A | 5/1994 | Lizardi et al. |
| 5,399,491 | A | 3/1995 | Kacian et al. |
| 5,445,933 | A * | 8/1995 | Eadie et al. ............... 435/6 |
| 5,487,972 | A | 1/1996 | Gelfand et al. |
| 5,514,546 | A | 5/1996 | Kool |
| 5,573,906 | A | 11/1996 | Bannwarth et al. |
| 5,607,834 | A | 3/1997 | Bagwell |
| 5,691,146 | A | 11/1997 | Mayrand |
| 5,723,591 | A | 3/1998 | Livak et al. |
| 5,731,148 | A | 3/1998 | Becker et al. |
| 5,804,375 | A | 9/1998 | Gelfand et al. |
| 5,827,649 | A | 10/1998 | Rose et al. |
| 5,866,336 | A | 2/1999 | Nazarenko et al. |
| 5,925,517 | A | 7/1999 | Tyagi et al. |
| 5,928,862 | A | 7/1999 | Morrison |
| 5,958,700 | A | 9/1999 | Nadeau et al. |
| 6,117,635 | A | 9/2000 | Nazarenko et al. |
| 6,355,421 | B1 | 3/2002 | Coull et al. |

OTHER PUBLICATIONS

Hyrup et al., "Peptide Nucleic Acids (PNA): Synthesis, Properties and Potential Applications", Bioorganic & Medicinal Chemistry, Jan. 1996, pp. 5–23, vol. 4, No. 1, Elsevier Science Ltd., GB.

Kostrikis et al., "Spectral Genotyping of Human Alleles", Science, Feb. 1998, pp. 1228–1229, vol. 279, No. 5354, American Association for the Advancement of Science, US.

Kramer et al., "Replicatable RNA Reporter", Nature, Jun. 1989, pp. 401–402, vol. 339, No. 6223, Macmillan Magazines Ltd., GB.

Lee et al., "Allelic discrimination by nick–translation PCR with fluorogenic probes", Nucleic Acids Research, Aug. 1993, pp. 3761–3766, vol. 21, No. 16, Oxford University Press, GB.

Leone et al., "Molecular beacon probes combined with amplification by NASBA enable homogeneous, real–time detection of RNA", Nucleic Acids Research, May 1998, pp. 2150–2155, vol. 26 No. 9, Oxford University Press, GB.

Livak et al., "Oligonucleotides with Fluorescent Dyes at Opposite Ends Provide a Quenched Probe System Useful for Detecting PCR Product and Nucleic Acid Hybridization", PCR Methods and Applications, Jun. 1995, pp. 357–362, vol. 4, No. 6, Cold Spring Harbor Laboratory Press, US.

Mergny et al., "Fluorescence energy transfer as a probe for nucleic acid structures and sequences", Nucleic Acids Research, Mar. 1994, pp. 920–928, vol. 22, No. 6, Oxford University Press, GB.

Morrison et al., "Solution–Phase Detection of Polynucleotides Using Interacting Fluorescent Labels and Competitive Hybridization", Analytical Biochemistry, Dec. 1989, pp. 231–244, vol. 183, No. 2, Academic Press, Inc., US.

Morrison et al., "Sensitive Fluorescence–Based Thermodynamic and Kinetic Measurements of DNA Hybridization in Solution", Biochemistry, Mar. 1993, pp. 3095–3104, vol. 32, No. 12, American Chemical Society, US.

Ortiz et al., "PNA molecular beacons for rapid detection of PCR amplicons", Molecular and Cellular Probes, Aug. 1998, pp. 219–226, vol. 12, No. 4, Academic Press, GB.

Packard et al., "Profluorescent protease substrates: Intramolecular dimers described by the exciton model", Proc. Natl. Acad. Sci., Oct. 1996, pp. 11640–11645, vol. 93, No. 21, The National Academy of Sciences, US.

Piatek et al., "Molecular beacon sequence analysis for detecting drug resistance in Mycobacterium tuberculosis", Nature Biotechnology, Apr. 1998, pp. 359–363, vol. 16, No. 4, Nature Publishing Co., US.

Tyagi et al., "Molecular Beacons: Probes that Fluoresce upon Hybridization", Nature Biotechnology, Mar. 1996, pp. 303–308, vol. 14, No. 3, Nature Publishing Co., US.

Tyagi et al., "Multicolor molecular beacons for allele discrimination", Nature Biotechnology, Jan. 1998, pp. 49–53, vol. 16, No. 1, Nature Publishing Co., US.

Varani, "Exceptionally Stable Nucleic Acid Hairpins", Annu. Rev. Biophys. Biomol. Struct., 1995, pp. 379–404, vol. 24, Annual Reviews Inc., US.

* cited by examiner

STRAND 1

5'-F-*cagugcaggnggaaag*-PEG-*ggcuggacugcgugcg*-3'-ccc
    (SEQ ID. NO. 1)        (SEQ ID. NO. 2)

STRAND 2

5'-F-*cagugcaggggaaag*-PEG-*ggcuggacugcgugcg*-3'-ccc
    (SEQ ID NO: 3)        (SEQ ID NO: 2)

STRAND 3

3'-Q-gtc<u>t</u>cgt<u>t</u>cc<u>t</u>tttc-PEG-*ccgaccugacgcacgc*-5'
    (SEQ ID NO: 4)        (SEQ ID NO: 5)

STRAND 4

3'Q-gtcanncgtccccnntttc-PEG-*ccgaccugacgcacgc*-5'
    (SEQ ID NO: 6)        (SEQ ID NO: 5)

FIG. 6A

TORCH 1

5'-F-*cagugcaggggaaag*-PEG-*ggcuggacugcgugcg*-3'-ccc
3'-Q-gtc<u>t</u>cgt<u>t</u>cc<u>t</u>tttc-PEG-*ccgaccugacgcacgc*-5'

TORCH 2

5'-F-*cagu--gcagggg--aaag*-PEG-*ggcuggacugcgugcg*-3'-ccc
3'-Q-gtcanncgtccccnntttc-PEG-*ccgaccugacgcacgc*-5'

TORCH 3

5'-F-*cagugcaggnggaaag*-PEG-*ggcuggacugcgugcg*-3'-ccc
3'-Q-gtc<u>t</u>cgt<u>t</u>c-c<u>t</u>tttc-PEG-*ccgaccugacgcacgc*-5'

TORCH 4

5'-F-*cagu--gcaggngg--aaag*-PEG-*ggcuggacugcgugcg*-3'-ccc
3'-Q-gtcanncgtcc-ccnntttc-PEG-*ccgaccugacgcacgc*-5'

TORCH 5

5'-F-*cagugcaggggaaag*-tttctttctttt-*ggcuggacugcgugcg*-3'-ccc
3'-Q-gtc<u>t</u>cgt<u>t</u>cc<u>t</u>tttc-ctttcttctttt-*ccgaccugacgcacgc*-5'

TORCH 6

5'-F-*cagugcaggggaaag* ⎤
3'-Q-gtc<u>t</u>cgt<u>t</u>cc<u>t</u>tttc ⎦ PEG

FIG. 6B

MOLECULAR TORCHES

This application is a continuation of U.S. application Ser. No. 09/346,551, filed Jul. 1, 1999, now U.S. Pat. No. 6,361,945, the contents of which are hereby incorporated by reference in their entirety, which claims the benefit of U.S. Provisional Application No. 60/091,616, filed Jul. 2, 1998.

FIELD OF THE INVENTION

The present invention relates to methods and compositions for detecting the presence or amount of a target nucleic acid sequence in a sample.

BACKGROUND OF THE INVENTION

None of the references described herein are admitted to be prior art to the claimed invention.

A target nucleic acid sequence can be detected by various methods using nucleic acid probes designed to preferentially hybridize to the target sequence over other sequences that may be present in a sample. Examples of target sequences include sequences that may be initially present in a sample, or produced as part of an amplification procedure, such as a sequence characteristic of a microorganism, a virus, a plant gene, or an animal gene such as a human gene. A reporter sequence which is produced as part of a detection method in the presence of a target sequence, but which has a sequence that is not dependent on the target sequence, can also be detected.

Hybridization of probes to target nucleic acid sequences can form detectable probe:target duplexes under appropriate conditions. Detection of such duplexes is facilitated using a labeled probe. Different techniques are available to reduce background due to signal from labeled probes not hybridized to a target sequence. Such techniques include using a physical separation step, a label preferentially altered in a probe:target duplex versus an unhybridized probe, and/or interacting labels.

Interacting labels are two or more labels which cooperate when in close proximity to one another to produce a signal which is different from a signal produced from such labels when they are farther apart so that their cooperation is diminished. The labels may be associated with one or more molecular entities. Detection systems can be designed such that the labels interact either in the presence of a target sequence or in the absence of a target sequence.

Taub et al., U.S. Pat. No. 4,820,630 describes interacting labels present on two different nucleic acid molecules cooperating to produce a detectable signal in the presence of a target nucleic acid sequence. Hybridization of both molecules to the target sequence brings the labels into close proximity so that they can cooperate to produce a signal different from labels not cooperating in close proximity.

Morrison, European Application Number 87300195.2, Publication Number 0 232 967, describes a detection system involving a reagent made up of two complementary nucleic acid probes. One of the complementary probes contains a first label, and the other complementary probe contains a second label. The first and the second labels can interact with each other. Formation of a complex between the target sequence and one of the two complementary probes changes the interaction between the two labels.

Lizardi et al., U.S. Pat. Nos. 5,118,801 and 5,312,728, describes a nucleic acid probe containing a target complementary sequence flanked by "switch" sequences that are complementary to each other. In the absence of a target sequence, the switch sequences are hybridized together. In the presence of a target sequence the probe hybridizes to the target sequence, mechanically separating the switch sequences and thereby producing an "open switch". The state of the switch sequence, whether open or closed, is indicated to be useful for selectively generating a detectable signal if the probe is hybridized to the target sequence.

Lizardi et al., International Application Number PCT/US94/13415, International Publication WO 95/13399, describes a "unitary" hybridization probe. The probe contains a target complementary sequence, an affinity pair holding the probe in a closed conformation in the absence of target sequence, and a label pair that interacts when the probe is in a closed conformation. Hybridization of the probe to the target sequence shifts the probe to an open conformation, which reduces the interaction between the label pair.

SUMMARY OF THE INVENTION

The present invention features "molecular torches" and the use of molecular torches for detecting the presence of a target nucleic acid sequence. Molecular torches contain a target binding domain, a target closing domain, and a joining region. The target binding domain is biased towards the target sequence such that the target binding domain forms a more stable hybrid with the target sequence than with the target closing domain under the same hybridization conditions. The joining region facilitates the formation or maintenance of a closed torch.

The presence of a target sequence can be detected using a molecular torch by measuring whether the molecular torch is opened or closed. In a "closed torch" the target binding domain is hybridized to the target closing domain. In an "open torch" the target binding domain is not hybridized to the target closing domain.

The target sequence bias of the molecular torch target binding domain, and the joining region, are preferably used to detect a target sequence in conjunction with (1) target binding domain denaturing conditions and target binding domain hybridizing conditions, or (2) strand displacement conditions.

Under target binding domain denaturing conditions the torch is open and readily accessible for hybridization to the target sequence. The target binding domain bias towards the target sequence allows the target binding domain to remain open in the presence of target sequence due to the formation of a target binding domain:target sequence hybrid even when the sample stringency conditions are lowered.

Under strand displacement conditions the target sequence can hybridize with the target binding domain present in a closed torch to thereby open the torch. Assays carried out using strand displacement conditions can be preformed under essentially constant environmental conditions. Under essentially constant environmental conditions the environment is not changed to first achieve denaturation and then achieve hybridization, for example, by raising and lowering the temperature.

The joining region facilitates the production or maintenance of a closed torch by producing at least one of the following: (1) an increase in the rate of formation of the closed torch; and (2) an increase in the stability of the closed torch. The increase in the rate of formation and/or stability is with respect to such activities in the absence of a joining region.

The joining region is made up of one or more groups that covalently and/or non-covalently link the target opening and target closing domains together. Individual groups present in the joining region are joined together by covalent and/or non-covalent interactions such as ionic interaction, hydrophobic interaction, and hydrogen bonding.

Detecting the presence of an open torch includes directly detecting whether open torches are present and/or detecting whether closed torches are present. Examples of techniques that can be used to detect open torches include the following: (1) those involving the use of interacting labels to produce different signals depending upon whether the torch is open or closed; (2) those involving the use of a target closing domain comprising a label that produces a signal when in a target binding domain:target closing domain hybrid that is different than the signal produced when the target closing domain is not hybridized to the target binding domain; and (3) those involving the detection of sequence information made available by an open target binding domain.

Preferably, interacting labels are used for detecting the presence of an open torch. Techniques involving the use of interacting labels can be carried out using labels that produce a different signal when they are positioned in close proximity to each other due to a closed target binding domain than when they are not in close proximity to each other as in an open target binding domain. Examples of interacting labels include enzyme/substrates, enzyme/cofactor, luminescent/quencher, luminescent/adduct, dye dimers, and Förrester energy transfer pairs.

The target binding domain and the target closing domains are made up of nucleotide base recognition sequences that are substantially complementary to each other. A "nucleotide base recognition sequence" refers to nucleotide base recognition groups covalently linked together by a backbone. Nucleotide base recognition groups can hydrogen bond, at least, to adenine, guanine, cytosine, thymine or uracil. A nucleotide base recognition sequence "backbone" is made up of one or more groups covalently joined together that provide the nucleotide base recognition groups with the proper orientation to allow for hybridization to complementary nucleotides present on nucleic acid.

"Substantially complementary sequences" are two nucleotide base recognition sequences able to form a stable hybrid under conditions employed. Substantially complementary sequences may be present on the same or on different molecules.

Substantially complementary sequences include sequences fully complementary to each other, and sequences of lesser complementarity, including those with mismatches and with linkers. Bugles, such as those due to internal non-complementary nucleotides, and non-nucleotide linkers, placed between two recognition groups hybridized together may also be present. Preferably, substantially complementary sequences are made up of two sequences containing regions that are preferably at least 10, at least 15, or at least 20 groups in length. Preferably, at least 70%, at least 80%, at least 90%, or 100% of the groups present in one of the two regions hydrogen bond with groups present on the other of the two regions. More preferably, hydrogen bonding is between complementary nucleotide bases A-T, G-C, or A-U.

A "linker" refers to a chain of atoms covalently joining together two groups. The chain of atoms are covalently joined together and can include different structures such as branches and cyclic groups.

Thus, a first aspect of the present invention features the use of a molecular torch to determine whether a target nucleic acid sequence is present in a sample. The molecular torch comprises: (1) a target detection means for hybridizing to the target sequence, if present, to produce an open torch; (2) torch closing means for hybridizing to the target detecting means in the absence of the target sequence to provide a closed torch conformation; and (3) joining means joining the target detection means and the torch closing means. Detecting the presence of the open torch provides an indication of the presence of the target sequence.

"Target detection means" refers to material described in the present application and equivalents thereof that can hybridize to the target sequence and the torch closing means. The target detection means is biased toward the target sequence, as compared to the torch closing means, such that in the presence of the target sequence the target detection means preferentially hybridizes to the target sequence.

"Torch closing means" refers to material described in the present application and equivalents thereof that can hybridize to the target detection means to provide a closed torch.

"Joining means" refers to material described in the present application and equivalents thereof that join the target detection means and the torch closing means, and that facilitate the production or maintenance of a closed torch in the absence of a target sequence.

Another aspect of the present invention features the use of a molecular torch to determine whether a target sequence is present involving the following steps: (a) contacting a sample with a molecular torch containing a target binding domain and a target closing domain connected together by a joining region; and (b) detecting the presence of an open torch as an indication of the presence of the target sequence.

The target binding domain is biased towards the target sequence such that a target binding domain:target sequence hybrid is more stable than a target binding domain:target closing domain hybrid. If the target sequence is not present, the closed torch conformation is favored.

Before being exposed to the sample, the molecular torch target binding domain may be open or closed depending upon the environment where it is kept. Denaturing conditions can be used to open up the target binding domain. Preferably, denaturation is achieved using heat.

Alternatively, strand displacement conditions can be employed. If strand displacement conditions are employed, then the molecular torch does not need to be opened before binding the target sequence.

Another aspect of the present invention describes a method of detecting the presence of a target sequence where a mixture containing a sample and a molecular torch is first exposed to denaturing conditions and then exposed to hybridization conditions. The presence of an open torch is used an indication of the presence of the target sequence.

"Denaturing conditions" are conditions under which the target binding domain:target closing domain hybrid is not stable and the torch is open. In a preferred embodiment, the joining region remains intact under the denaturing conditions. Thus, in this preferred embodiment, under denaturing conditions the target binding domain becomes available for hybridization to the target sequence, but is also kept in proximity to the target closing domain for subsequent hybridization in the absence of the target sequence.

"Hybridization conditions" are conditions under which both the target binding domain:target closing domain hybrid and the target binding domain:target sequence hybrid are stable. Under such conditions, in the absence of the target sequence, the target binding domain is not inhibited by hybridized target sequence from being present in a hybrid with the target closing domain.

Another aspect of the present invention describes a molecular torch. The molecular torch contains (1) a target detection means for hybridizing to a target sequence, if present, to produce an open torch; (2) a torch closing means for hybridizing to the target detecting means in the absence of the target sequence to provide a closed torch; and (3) a joining means for facilitating a closed torch conformation in the absence of the target sequence.

Another aspect of the present invention describes a molecular torch containing a target binding domain and a target closing domain joined together through a joining region. The target binding and target closing domains are substantially complementary to each other. The target binding domain is biased to a target sequence that is a perfect DNA or RNA complement, preferably RNA complement, of the target binding domain. Thus, the target binding domain forms a more stable duplex with its prefect DNA or RNA complement than with the target closing domain.

A "perfect DNA or RNA complement of the target binding domain" is a DNA or RNA containing a complementary purine or pyrimidine nucleotide base opposite each recognition group present in the target binding domain. The complementary purine or pyrimidine nucleotide bases can hydrogen bond to each other.

Various examples are described herein. These examples are not intended in any way to limit the claimed invention.

Other features and advantages of the invention will be apparent from the following drawing, the description of the invention, the examples, and the claims.

BRIEF DESCRIPTION OF THE DRAWINGS

FIGS. 6A and 6B illustrate strands making up molecular torches 1–7. "F" refers to a fluorophore, "Q" refers to a quencher, "PEG" refers to polyethylene glycol, and "ccc" refers to a propyl group located at the 3'-position of the terminal sugar. Bases shown in italics are 2'-methoxy substituted ribonucleotides.

DETAILED DESCRIPTION OF THE INVENTION

A molecular torch is preferably designed to provide favorable kinetic and thermodynamic components in an assay to detect the presence of a target sequence. The kinetic and thermodynamic components of an assay involving a molecular torch can be used to enhance the specific detection of a target sequence.

Figure 1:
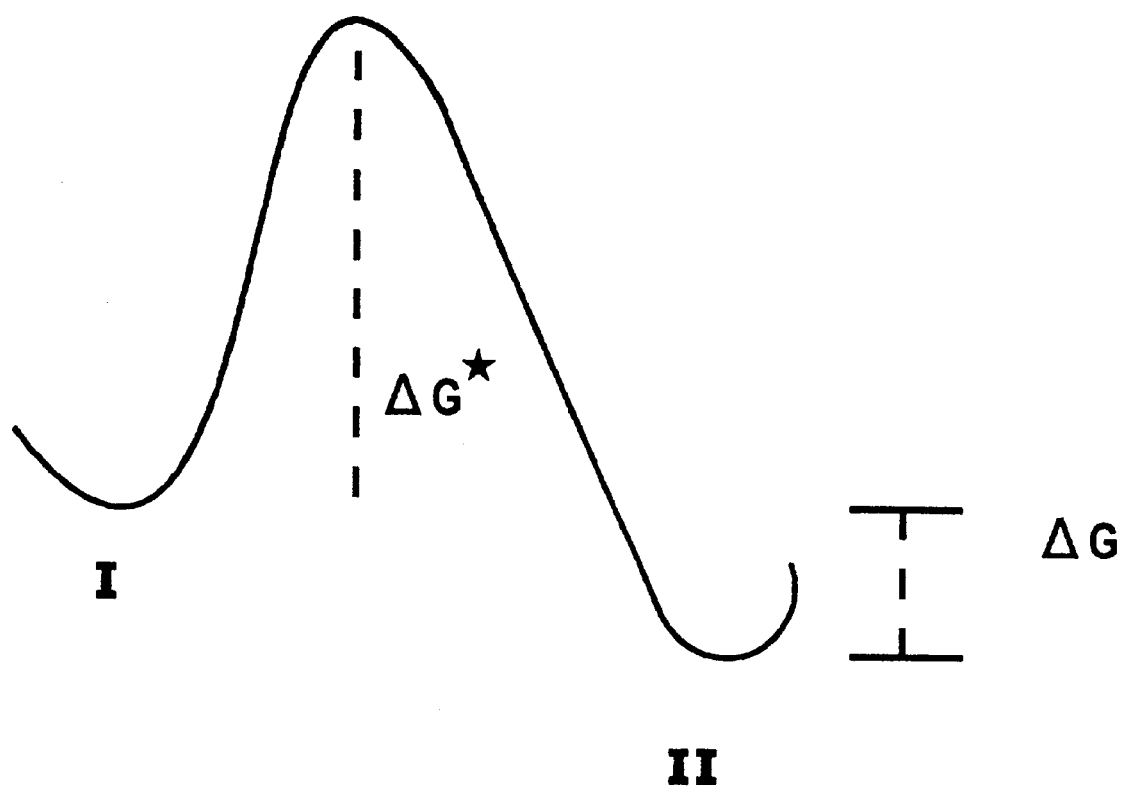
FIG. 1 provides an energy diagram illustrating the free energy of a target binding domain:target closing domain hybrid (I), the stability of a target binding domain:target sequence hybrid (II), the difference in the free energy of I and II ($\Delta G$), and the difference in the activation free energy ($\Delta G^*$) for the conversion of I into II.

The thermodynamics of a preferred molecular torch are illustrated in FIG. 1. Referring to FIG. 1, "I" denotes the target binding domain:target closing domain hybrid while "II" denotes the target binding domain:target sequence hybrid. In FIG. 1, $\Delta G^*$ represents the free energy of activation required to melt the target binding domain:target closing domain, and $\Delta G$ represents the difference in free energy between the target binding domain:target closing domain hybrid and the target binding domain:target sequence hybrid.

The thermodynamic component of the present invention is based upon the target binding domain:target sequence hybrid being more stable than the target binding domain:target closing domain hybrid ($\Delta G<0$). The joining region facilitates the closed torch conformation in the absence of the target sequence.

Additionally, depending upon the torch design, the joining region can be used to provide one or more of the following advantages: (1) reducing the probability of labels present on the target opening and closing domains coming apart in the absence of target; (2) facilitating the use of short target binding domains which can be used to enhance its sensitivity to mismatched targets; (3) facilitating a closed torch conformation when the target closing domain and the target binding domain contains, for example, mismatches or abasic "nucleotides"; and (4) facilitating the detection of adenine and thymine rich target sequences by stabilizing interaction of adenine and thymine rich target binding and target closing domains.

Denaturing Conditions

Denaturing conditions can be used to provide sufficient energy ($\Delta G^*$) to melt the target binding domain:target closing domain hybrid. The amount of energy required will vary depending upon the molecular torch composition and the environmental conditions. The environmental conditions include the assay solution composition and temperature. The necessary energy needed to open a closed target can be supplied, for example, by heating the sample.

A useful measure of the stability of a hybrid is the melting temperature ($T_m$). At the melting temperature 50% of the hybrids present are denatured.

Using a particular assay composition, a hybrid is not stable when the assay temperature is above the $T_m$. Depending upon the composition of an assay, the $T_m$ of a hybrid will vary. Factors such as salt concentration and the presence of denaturing agents can affect the $T_m$ of a given hybrid. The $T_m$ is determined using a particular assay composition and varying the temperature.

By taking into account factors affecting $T_m$, such as those described herein and those well known in the art, molecular torches can be readily designed to have a desirable target binding domain:target closing domain $T_m$ and a desirable target binding domain:target $T_m$ such that $\Delta G<0$. The $T_m$ can be measured, for example, using techniques such as those described by Sambrook et al., Molecular Cloning a Laboratory Manual, Second ed., Cold Spring Harbor Laboratory Press, 1989, and Hogan et al., U.S. Pat. No. 5,547,842 (both of which are hereby incorporated by reference herein).

While FIG. 2 shows a number of different molecular torch configurations, those skilled in the art will readily appreciate other molecular torch configurations which may be used in practicing the present invention. FIG. 2A illustrates a two-stranded molecular torch made up of a target binding region and a joining region. The target binding region consists of a target binding domain that binds the target sequence and a target closing domain that binds the target binding domain.

Figure 2A:
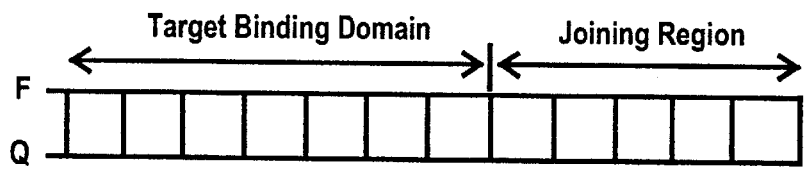
FIGS. 2A–2G provides examples of different molecular torch structures. "F" refers to fluorophore and "Q" refers to quencher.
Figure 2B:
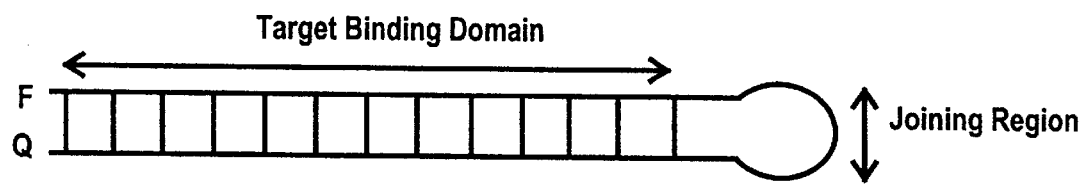
Figure 2C:
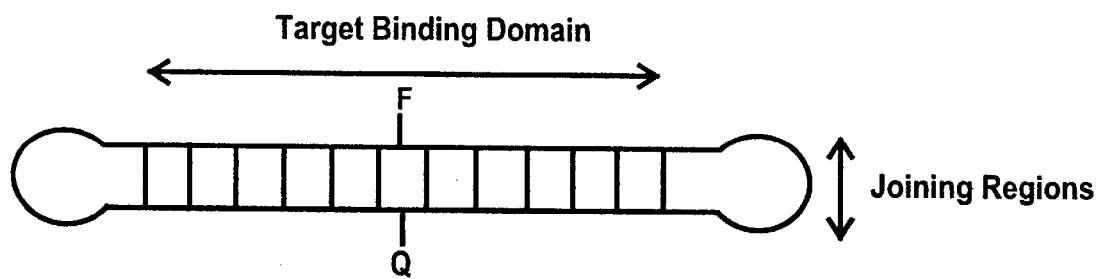
Figure 2D:
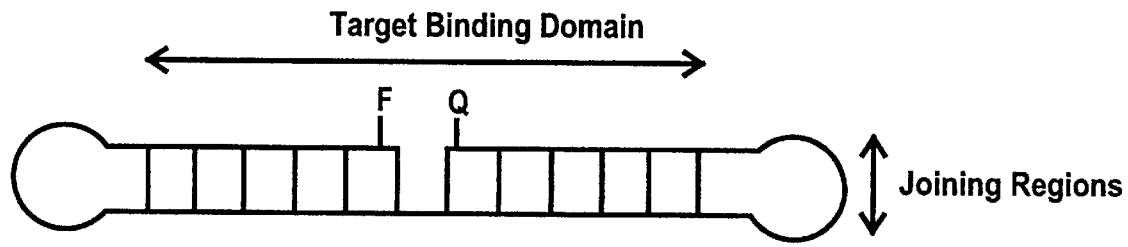
Figure 2E:
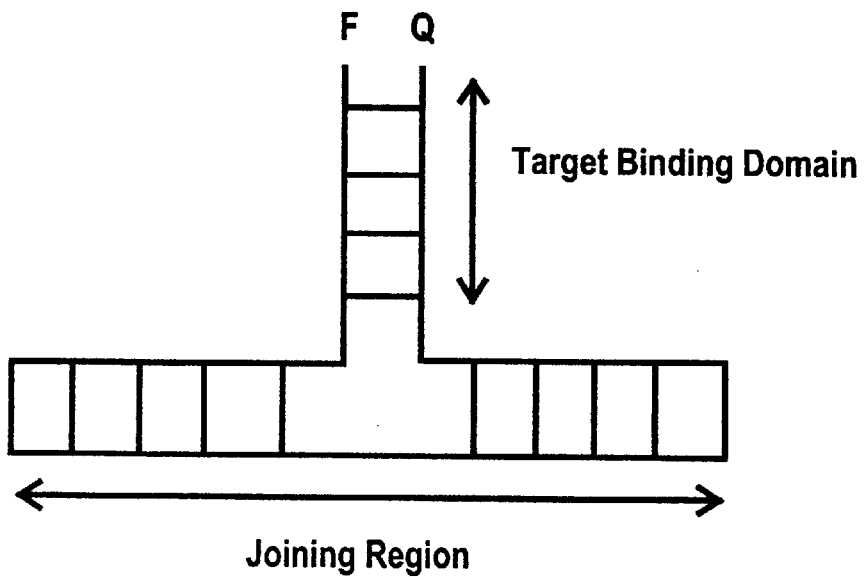

FIGS. 2B–2D illustrate single-stranded molecular torches composed of target binding and joining regions, while FIG. 2E illustrates a three-stranded molecular torch.

Figure 2F:
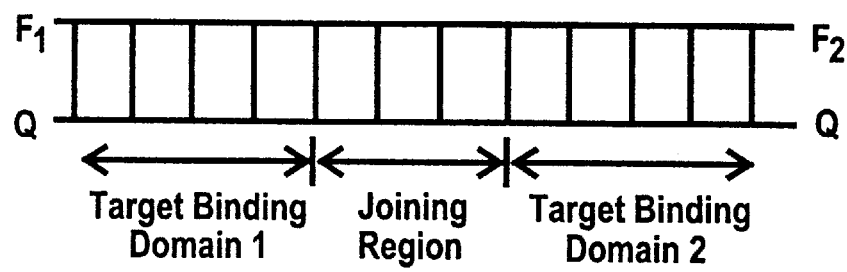

FIG. 2F illustrates a molecular torch containing a joining region and two target binding regions. The two target binding regions can bind the same or different target sequences and can have the same or different interacting labels. For example, by positioning different types of fluorophores having different emission characteristics that are separately detectable on each target binding region the presence of different target sequences can be detected using a single molecular torch by looking for the signal characteristics of the different fluorophores.

Figure 2G:
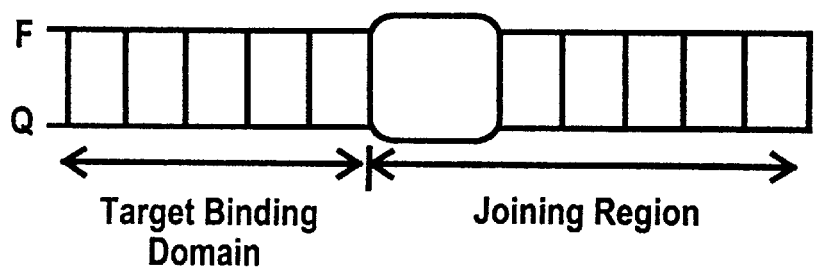

FIG. 2G illustrates a two-stranded molecular torch made up of a target binding region and a joining region. The joining region contains complementary polynucleotides joined to the target binding or target closing domains by a linker made up, for example, of PEG or a polynucleotide.

Strand Displacement Conditions

Under strand displacement conditions the target binding domain:target sequence hybrid is more stable than the target binding domain:target closing domain hybrid, and production of the target binding domain:target sequence hybrid is favored if the target sequence is present.

Strand displacement is preferably performed using torches having nucleotide base recognition groups accessible for hybridization to target. Such torches preferably contain one to about ten nucleotide base recognition groups complementary to the target sequence which are accessible. Preferably, no more than ten, five or three nucleotide base recognition groups are accessible.

Different configurations are possible, including those where the single-stranded region is a terminal region, or where the single-stranded region is an internal region such as a loop region. Alternatively, strand displacement conditions causing, for example, the 5' or 3' terminal torch region to "breath" may be employed. Breathing of a torch occurs under conditions where the stability of a region allows the torch to become single-stranded and hybridize to the target sequence such that formation of the target binding domain-:target sequence hybrid is favored.

Figure 3A:
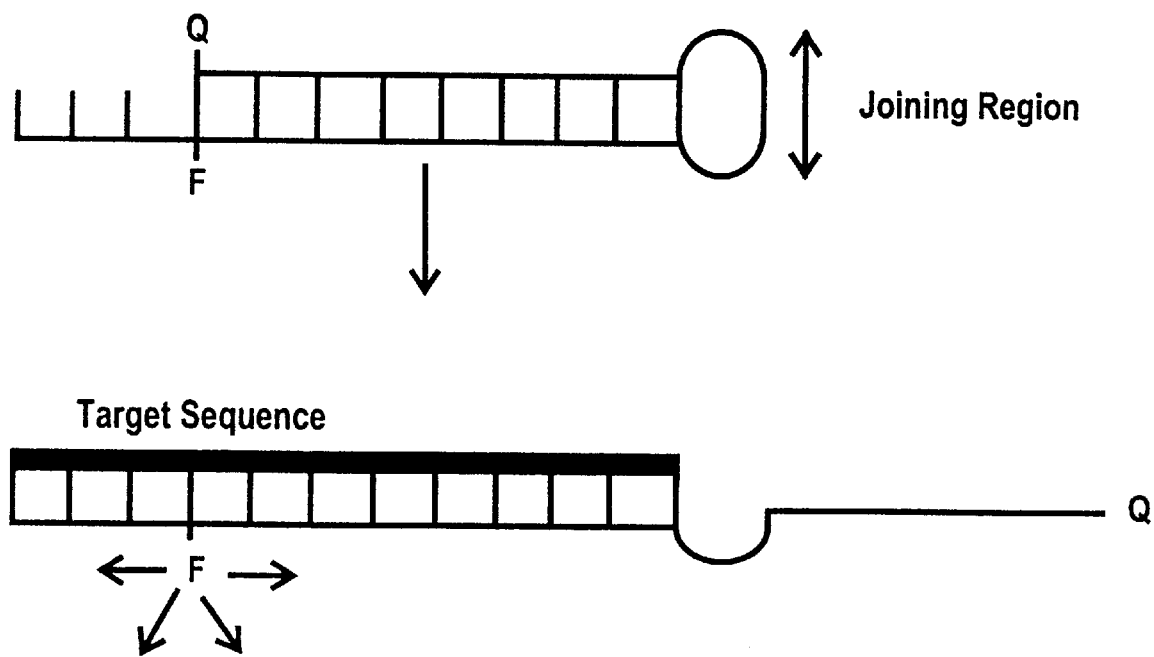
FIGS. 3A–3C provide examples of strand displacement. "F" refers to fluorophore and "Q" refers to quencher. Target sequence is shown by a bolded line.
Figure 3B:
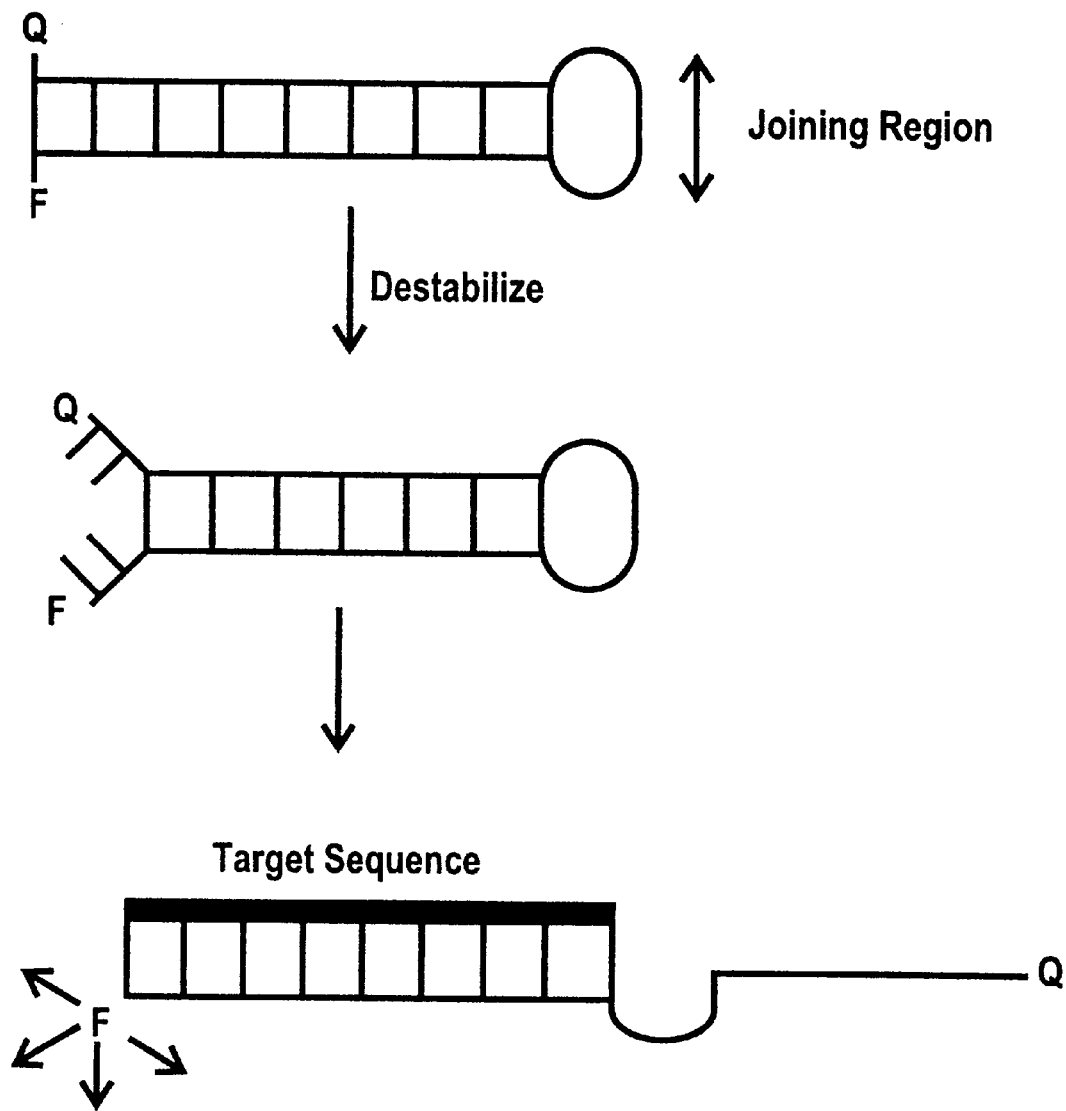
Figure 3C:
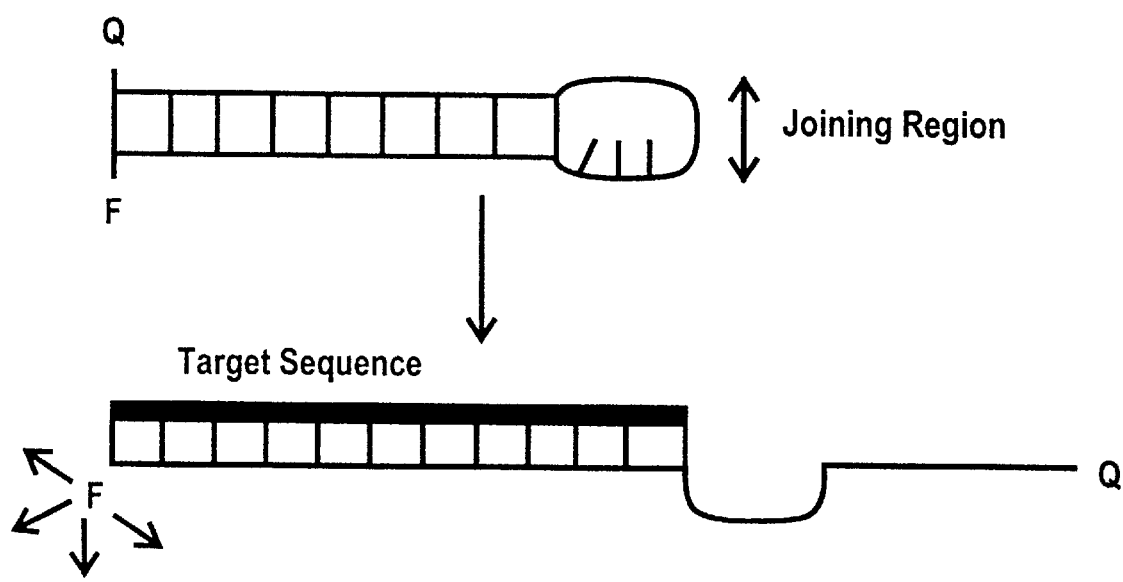

FIGS. 3A–3C provides different examples of strand displacement. FIGS. 3A and 3C illustrate molecular torches having three terminal nucleotides available for target hybridization. FIG. 3B illustrates breathing of two terminal nucleotides and target hybridization.

Target Sequence Bias

The target binding domain can be biased towards the target sequence using different design considerations affecting nucleic acid hybrid stability. Such considerations include the degree of complementarity, the type of complementary recognition groups, and the nucleotide base recognition sequence backbone. The affect of these different factors varies depending upon the environmental conditions.

The degree of complementarity takes into account the number of recognition groups present on the target binding domain that hydrogen bond with recognition groups present on the target closing domain and with the target sequence. The target binding domain can be designed to have a greater degree of complementarity to the target sequence than to the target closing domain using different techniques. Such techniques include, for example, designing the target binding domain to have mismatches with the target closing domain but not the target sequence and the use of non-nucleotide linkers in the target closing domain.

Examples of non-nucleotide linkers present in a nucleotide base recognition sequence are abasic "nucleotides". Abasic "nucleotides" lack a nucleotide base recognition group.

Other examples of non-nucleotide linkers include polysaccharides, peptides, and polypeptides. Arnold et al. International Application No. PCT/US88/03173, International Publication WO 89/02439, and U.S. Pat. No. 5,585,481, hereby incorporated by reference herein, also provide examples of non-nucleotide linkers.

The types of recognition groups present can be used to bias the target binding domain towards the target sequence by taking into account factors such as the degree of hydrogen bonding between different nucleotide purine and pyrimidine bases. For example, G-C pairing or 2,6 diaminopurine-thymine is stronger than A-T pairing and pairing with universal bases such as inosine. The target binding domain can be designed to have increased G or C pairing with nucleotides present in a target sequence compared to the target closing domain.

The composition of nucleotide base recognition sequence backbones can be adjusted in different ways to bias the target binding domain towards a target sequence. Preferred molecular torch backbones are sugar-phosphodiester type linkages, such as those present in ribo- and deoxyribonucleic acids. Another type of linkage is a peptide linkage, such as that present in peptide nucleic acids.

Peptide nucleic acids generally form a more stable duplex with RNA than with the corresponding DNA sequence. Thus, the target binding domain can be biased towards an RNA target sequence, for example, by using a molecular torch where the target binding domain contains peptide nucleic acid groups and the target closing domain is made up of DNA.

In the case of a sugar-phosphodiester type linkage, both the sugar group and the linkage joining two sugar groups will affect hybrid stability. An example of the affect the sugar can have is that seen with 2'-methoxy substituted RNA. 2'-methoxy containing nucleic acids generally form more stable duplexes with RNA than with the corresponding DNA sequence. Another example, is 2'-fluoro substituted RNA that has the same type of affect as 2'-methoxy substituted RNA.

Examples of ways in which the backbone linking group may affect hybrid stability include affecting the charge density and the physical association between two strands. Steric interactions from bulky groups can reduce hybrid stability. Groups such as phosphorothioates can reduce hybrid stability, whereas uncharged groups such as methylphosphonates can increase hybrid stability.

Target Binding Domain:Target Sequence Hybrid

Formation of a target binding domain:target sequence hybrid results in the production of an open torch that is more stable than a closed torch. Conditions for opening up of the torch, or strand displacement, can be used to facilitate the production of an open torch in the presence of a target sequence.

Opening and closing of the torch can be achieved by changing the environmental conditions of the detection method employed. Examples of changes to the environmental conditions to open and close the torch include heating and cooling; raising and lowering the pH; and adding a denaturing agent, then diluting out the agent.

The target binding domain:target sequence hybrid is more stable than the target binding domain:target closing domain hybrid. Preferably, under conditions used in the detection method, the target binding domain:target $T_m$ is at least 2° C., more preferably at least 5° C., even more preferably at least 10° C., more than the target binding domain:target closing domain $T_m$.

A closed torch in the absence of a target sequence reduces background from a molecular torch not hybridized to the target sequence without the need for a separation step. Preferably, in those assays where the torch is first opened, hybridization conditions closing the torch in the absence of a target sequence employ a temperature that is at least 2° C. lower, more preferably at least 5° C. lower, and more preferably at least 10° C. lower, than the $T_m$ of the target binding domain:target closing domain hybrid.

If desired, a separation step can be employed to physically separate molecular torches hybridized to target sequences from molecular torches not hybridized to target sequences. A separation step can be carried out, for example, using sequence information made available by the open target binding domain. For example, a capture probe having a nucleic acid sequence complementary to the target closing domain can be used to capture a molecular torch hybridized to a target sequence. The capture probe itself may be provided either directly or indirectly on a bead or column.

If capture probes, or other types of nucleic acid probes complementary to the target closing domain are used, it is important that such probes be designed and used under conditions where a stable target closing domain:probe hybrid is not formed in the absence of a target binding domain:target sequence hybrid. Preferably, a target closing domain:probe hybrid has a $T_m$ that is at least 5° C., and more preferably at least 10° C. lower than a target binding domain:target closing domain hybrid.

Detecting the Target Sequence

Molecular torches can be used to detect the presence of a target sequence by determining whether the torch is open under conditions where a target binding domain:target closing domain hybrid is stable. Open torches can be detected using different techniques such as (1) those involving the use of interacting labels to produce different signals depending upon whether the torch is open or closed; (2) those involving the use of a target closing domain comprising a label that produces a signal when in a target binding domain:target closing domain hybrid that is different from the signal produced when the target closing domain is not hybridized to the target binding domain; and (3) those involving the detection of sequence information made available by an open target binding domain.

Different types of interacting labels can be used to determine whether a torch is open. Preferably, the interacting labels are either a luminescent/quencher pair, luminescent/adduct pair, Förrester energy transfer pair or a dye dimer. More than one label, and more than one type of label, may be present on a particular molecule.

A luminescent/quencher pair is made up of one or more luminescent labels, such as chemiluminescent or fluorescent labels, and one or more quenchers. Preferably, a fluorescent/quencher pair is used to detect an open torch. A fluorescent label absorbs light of a particular wavelength, or wavelength range, and emits light with a particular emission wavelength, or wavelength range. A quencher dampens, partially or completely, signal emitted from an excited fluorescent label. Quenchers can dampen signal production from different fluorophores. For example, 4-(4'-dimethyl-aminophenylaxo)benzoic acid (DABCYL) can quench about 95% of the signal produced from 5-(2'-aminoethyl) aminoaphthaline-1-sulfonic acid (EDANS), rhodamine and fluorescein.

Different numbers and types of fluorescent and quencher labels can be used. For example, multiple fluorescent labels can be used to increase signal production from an opened torch, and multiple quenchers can be used to help ensure that in the absence of a target sequence an excited fluorescent molecule produces little or no signal. Examples of fluorophores include acridine, fluorescein, sulforhodamine 101, rhodamine, EDANS, Texas Red, Eosine, Bodipy and lucifer yellow. (E.g., see Tyagi et al., Nature Biotechnology 16:49–53, 1998, hereby incorporated by reference herein). Examples of quenchers include DABCYL, Thallium, Cesium, and p-xylene-bis-pyridinium bromide.

A luminescent/adduct pair is made up of one or more luminescent labels and one or more molecules able to form an adduct with the luminescent molecule(s) and, thereby, diminish signal production from the luminescent molecule(s). The use of adduct formation to alter signals from a luminescent molecule using ligands free in solution is described by Becker and Nelson, U.S. Pat. No. 5,731,148, hereby incorporated by reference herein. Adducts can also be formed by attaching an adduct former to the molecular torch, or to a nucleic acid probe that hybridizes with sequence information made available in an open torch.

Förrester energy transfer pairs are made up of two labels where the emission spectra of a first label overlaps with the excitation spectra of a second label. The first label can be excited and emission characteristic of the second label can be measured to determine if the labels are interacting. Examples of Förrester energy transfer pairs include pairs involving fluorescein and rhodamine; nitrobenz-2-oxa-1,3-diazole and rhodamine; fluorescein and tetramethylrhodamine; fluorescein and fluorescein; IAEDANS and fluorescein; and BODIPYFL and BIODIPYFL.

A dye dimer is made up of two dyes that interact upon formation of a dimer to produce a different signal than when the dyes are not in a dimer conformation. Dye dimer interactions are described, for example, by Packard et al., Proc. Natl. Sci. USA 93:11640 –11645, 1996 (which is hereby incorporated by reference herein).

The observed signal produced during the detection step that is characteristic of the presence of a target sequence can be compared against a control reaction having no target sequence or known amounts of target sequences. Known amounts of target sequences can be used to obtain a calibration curve. While a control reaction is preferably performed at the same time as an experimental reaction, control reactions do not need to be run at the same time as the experimental reaction and can be based on data obtained from a previous experiment.

Figure 4:
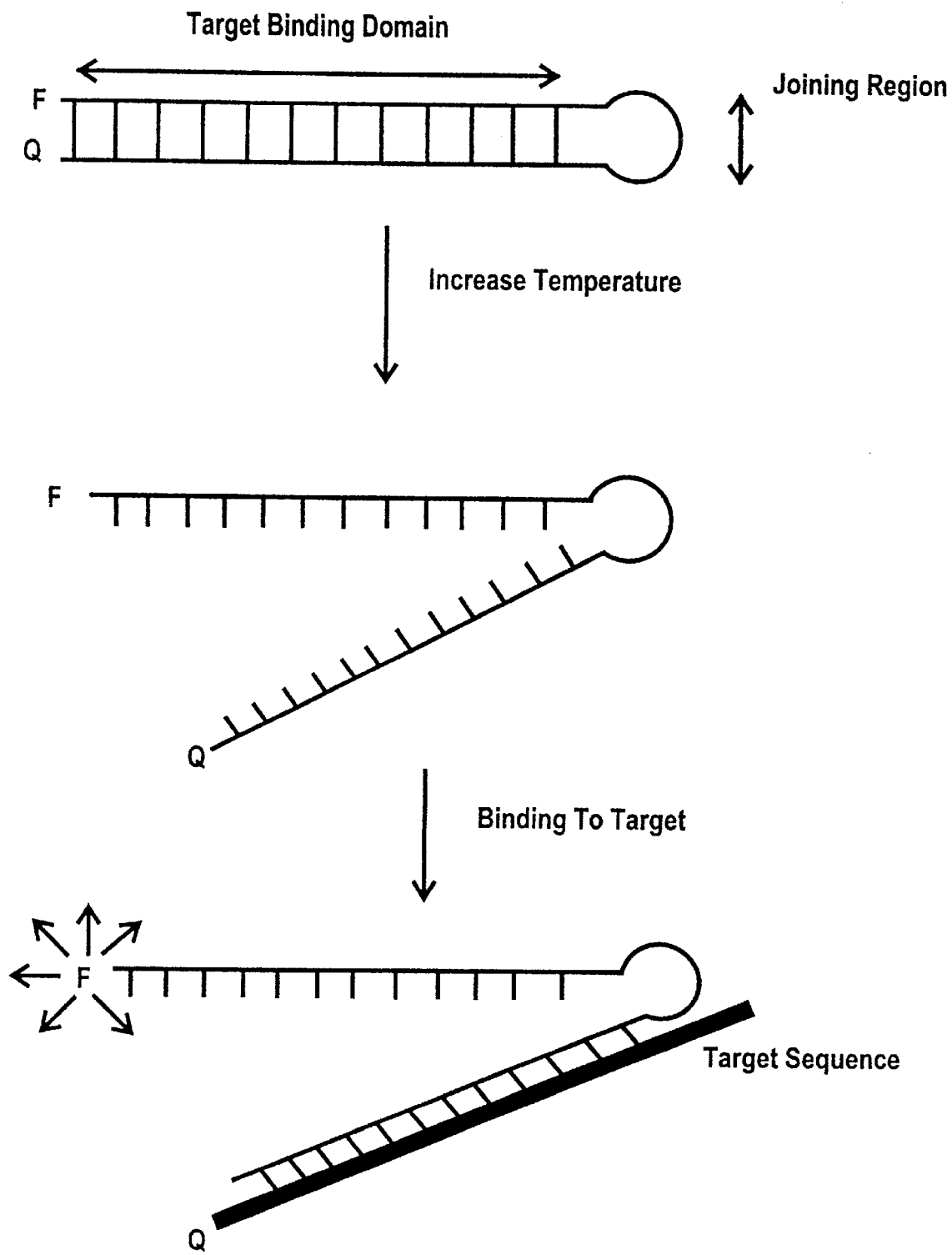
FIG. 4 illustrates the functioning of a molecular torch containing a joining region that is a covalent linkage. "F" refers to fluorophore and "Q" refers to quencher.
Figure 5:
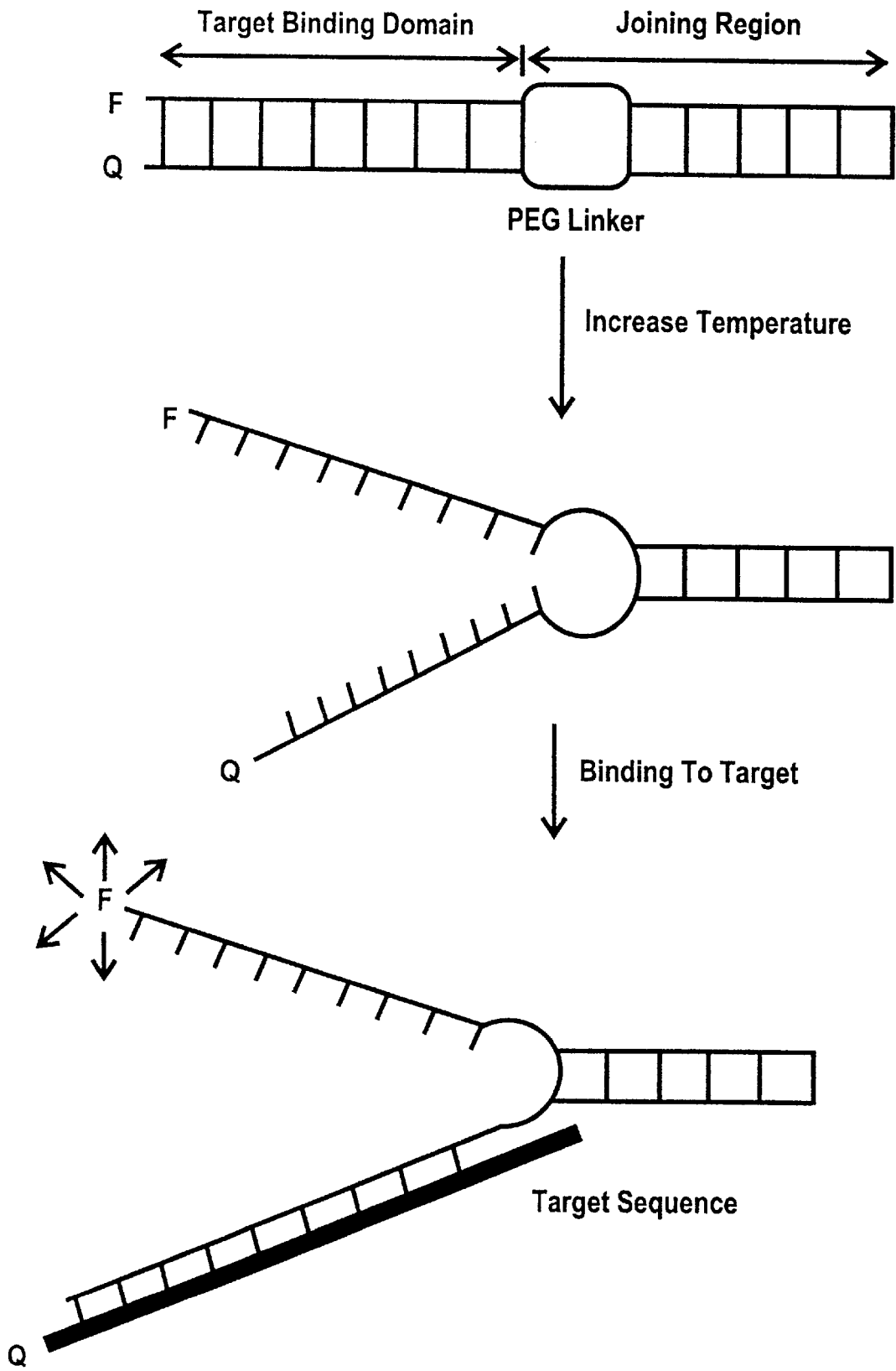
FIG. 5 illustrates the functioning of a molecular torch containing a joining region made up of two polyethylene glycol (PEG) groups and two substantially complementary nucleic acid sequences having a sufficiently high $T_m$ so as not to melt during heating. "F" refers to fluorophore and "Q" refers to quencher.

Examples of using molecular torches having interacting labels to detect a target sequence are provided in FIGS. 4 and 5. Both figures illustrate the presence of a target sequence. In the absence of the target sequence, the molecular torch target binding domain is closed resulting in the quenching of signal.

FIG. 4 illustrates the use of a single-stranded molecular torch containing a small joining region. Heat is used to melt the target binding domain:target closing domain hybrid. The torch is biased towards an RNA target sequence by, for example, the presence of 2'-methoxy substituted ribonucleotides present in the target binding domain. In the presence of the target sequence the quencher (Q) is no longer held in close proximity to the fluorophore (F), thus, decreasing the ability of the quencher to affect fluorophore fluorescence.

FIG. 5 illustrates the use of a double-stranded molecule with a joining region made up of two parts, a non-nucleotide PEG linker and a sequence whose high $T_m$ prevents its melting during the assay.

Another embodiment of the present invention involves detecting open torches using a label producing a signal when in a target binding domain:target closing domain hybrid that is different from the signal produced when the target closing domain is not hybridized to the target binding domain. Such labels include luminescent molecules and labels having a different stability when present in different environments.

Signal produced from luminescent molecules present on one nucleotide base recognition sequence can be affected by another nucleotide base recognition sequence. For example, nucleotides on one nucleotide base recognition sequence can be used to quench, or effect the rotational motion, of a fluorophore present on another nucleotide base recognition sequence.

Environments that can affect the stability of certain labels include a nucleic acid duplex formed with Watson-Crick base pairing. Examples of such labels and there use are described by Becker and Nelson, U.S. Pat. No. 5,731,148, and Arnold et al., U.S. Pat. No. 5,283,174, both of which are hereby incorporated by reference herein.

Acridinium ester and derivatives thereof are preferred examples of labels for detecting open torches based on the environment of the label. An acridinium ester can be detected using different techniques such as selectively inactivating label not present in a nucleic acid duplex. An example of the use of one or more acridinium ester labels involves attaching such labels to the target closing domain and using a reduction in signal due to selective inactivation of acridinium ester label(s) present on a single-stranded target closing domain as an indication of the presence of target sequence.

The detection of open torches using sequence information made available by an open target binding domain can be carried out using detection probes that hybridize to the target closing domain. Preferred detection probes contain a detectable label. The detectable label can, for example, be a label interacting with a label present on the target closing domain, or can be a label that produces a signal in the absence of an interacting label on the target closing domain. A preferred probe label is an acridinium ester.

Increasing the Number of Target Sequences

In cases where a target sequence is present in a sample in low numbers, an amplification can be performed to increase the number of target sequences. Numerous amplification techniques are well known in the art including those involving transcription-associated amplification, the polymerase chain reaction (PCR) and the ligase chain reaction (LCR).

Preferably, the molecular torch is used in conjunction with a transcription-associated amplification. Transcription-associated amplification involves generating RNA transcripts using an RNA polymerase that recognizes a double-stranded DNA promoter region.

Examples of references describing transcription-associated amplification include Burg et al., U.S. Pat. No. 5,437,990; Kacian et al., U.S. Pat. No. 5,399,491; Kacian et al., U.S. Pat. No. 5,554,516; Kacian et al., International Application No. PCT/US93/04015, International Publication WO 93/22461; Gingeras et al., International Application No. PCT/US87/01966, International Publication WO 88/01302; Gingeras et al., International Application No. PCT/US88/02108, International Publication WO 88/10315; Davey and Malek, EPO Application No. 88113948.9, European Publication No. 0 329 822 A2; Malek et al., U.S. Pat. No. 5,130,238; Urdea, International Application No. PCT/US91/00213, International Publication WO 91/10746; McDonough et al., International Application No. PCT/US93/07138, International Publication WO 94/03472; and Ryder et al., International Application No. PCT/US94/08307, International Publication WO 95/03430. (Each of these references is hereby incorporated by reference herein.)

The use of a transcription-associated amplification procedure involving RNase H activity is preferred. More preferably, the procedure utilizes RNase H activity present in reverse transcriptase to facilitate strand separation. Kacian et al., U.S. Pat. No. 5,399,491 describes an amplification occurring under essentially constant conditions without the addition of exogenous RNase H activity. The procedure utilizes RNase H activity present in reverse transcriptase to facilitate strand separation.

One of the advantages of using the present invention in conjunction with a transcription-associated amplification is that the molecular torch can be added prior to amplification, and detection can be carried out without adding additional reagents. The molecular torch is well suited for use in a transcription-associated amplification because the $T_m$ of the target binding domain:target closing domain hybrid can readily be adjusted to be higher than the temperature used during the amplification. The closed target binding domain prevents the molecular torch from prematurely binding to target sequences generated by amplification.

After amplification, the solution can be heated to open the target binding domain allowing the molecular torch to hybridize to a target sequence. The solution can then be cooled to close target binding domains of torches not hybridized to target sequences. The presence of open torches having, for example, a fluorophore/quencher pair can then be measured by irradiating the sample with the appropriate excitation light and then measuring emission light.

Examples of references mentioning other amplification methods include those describing PCR amplification such as Mullis et al., U.S. Pat. Nos. 4,683,195, 4,683,202, and 4,800,159, and Methods in Enzymology, Volume 155, 1987, pp. 335–350; and those describing the ligase chain reaction, such as Backman, European Patent Application No. 88311741.8, European Publication No. 0 320 308. (Each of these references is hereby incorporated by reference herein.)

Molecular Torch Construction

A molecular torch comprises a target binding domain, a target closing domain and a joining region. The target binding and closing domains are each nucleotide base recognition groups.

Nucleotide base recognition sequences contain nucleotide base recognition groups able to hydrogen bond with nucleotide nitrogenous bases present in nucleic acid. The nucleotide base recognition groups are joined together by a backbone providing a proper conformation and spacing to allow the groups to hydrogen bond to nucleotides present on nucleic acid.

A given nucleotide base recognition group may be complementary to a particular nucleotide (e.g., adenine, guanine, cytosine, thymine, and uracil) and, thus, be able to hydrogen bond with that nucleotide present in a nucleic acid. A nucleotide base recognition group may also be able to hydrogen bond with different nucleotides. For example, when inosine is a nucleotide base recognition group it can hydrogen bond with different nucleotide bases.

Preferred nucleotide base recognition groups are nitrogenous purine or pyrimidine bases, or derivatives thereof, able to hydrogen bond with either adenine, guanine, cytosine, thymine or uracil. Examples of such recognition groups include adenine, guanine, cytosine, thymine, uracil, and derivatives thereof. Examples of derivatives include modified purine or pyrimidine bases such as N4-methyl deoxyguanosine, deaza or aza purines and pyrimidines used in place of natural purine and pyrimidine bases, pyrimidine bases having substituent groups at the 5 or 6 position, and purine bases having an altered or a replacement substituent at the 2, 6 or 8 position. See, e.g., Cook, International Application No. PCT/US92/11339, International Publication WO 93/13121 (hereby incorporated by reference herein). Additional examples include, 2-amino-6-methylaminopurine, O6-methylguanine, 4-thio-pyrimidines, 4-amino-pyrimidines, 4-dimethylhydrazine-pyrimidines and O4-alkyl-pyrimidines (see, e.g., The Glen Report volume 1, 1993).

The nucleotide base recognition sequence backbone can be made up of different groups. Examples of different backbones include a sugar-phosphodiester type backbone and a peptide nucleic acid backbone.

Structure I illustrates a sugar-phosphodiester type backbone where the sugar group is a pentofuranosyl group. The sugar groups are joined together by a linkage such as a phosphodiester linkage or other suitable linkage.

STRUCTURE I

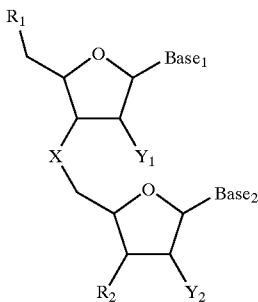

X represents the group joining two sugars. Examples of X include —OP(O)$_2$O—, —NHP(O)$_2$O—, —OC(O)$_2$O—, —OCH$_2$C(O)$_2$NH—, —OCH$_2$C(O)$_2$O—, —OP(CH$_3$)(O)O—, —P(S)(O)O— and —OC(O)$_2$NH—. As with the other examples provided herein, other equivalents that are well known in the art or which become available can also be used.

$Y_1$, and $Y_2$ are independently selected groups. Examples of $Y_1$, and $Y_2$ include H, OH, $C_1$–$C_4$ alkoxy, halogen, and $C_1$–$C_6$ alkyl. Preferably, $Y_1$, and $Y_2$ are independently either H, OH, F, or OCH$_3$. $C_1$–$C_6$ alkyl and $C_1$–$C_4$ alkoxy, may be or may include groups which are, straight-chain, branched, or cyclic.

Base$_1$, and Base$_2$ are independently selected from the group consisting of: adenine, guanine, cytosine, thymine, uracil, or a group that does not inhibit complementary base pairing of an adjacent base to a complementary nucleic acid. Examples, of groups not inhibiting complementary base pairing include smaller size groups such as hydrogen, OH, $C_1$–$C_6$ alkyl, and $C_1$–$C_4$ alkoxy. Preferably, the nucleotide base recognition sequence contains about 7 to about 40, more preferably, about 10 to about 30, bases independently selected from the group consisting of: adenine, guanine, cytosine, thymine, and uracil.

$R_1$ and $R_2$ represent independently selected groups. Examples of $R_1$ and $R_2$ include additional sugar-phosphodiester type groups, hydrogen, hydroxy, peptide nucleic acid, and molecules not providing sequence information such as abasic "nucleotides", polysaccharides, polypeptides, peptides, and other non-nucleotide linkages.

Derivatives of Structure I able to be a component of a nucleotide base recognition sequence are well known in the art and include, for example, molecules having a different type of sugar. For example, a nucleotide base recognition sequence can have cyclobutyl moieties connected by linking moieties, where the cyclobutyl moieties have heterocyclic bases attached thereto. See, e.g., Cook et al., International Application No. PCT/US93/01579, International Publication WO 94/19023 (hereby incorporated by reference herein).

In an embodiment of the present invention, a nucleotide base recognition molecule is a polynucleotide or derivative thereof. A "polynucleotide or derivative thereof" is a nucleotide base recognition molecule made up of structure I repeating units where X is —OP(O)$_2$O—; $Y_1$, and $Y_2$ are independently selected groups from the group consisting of H, OH, OCH$_3$, and F; Base$_1$, and Base$_2$ are independently selected from the group consisting of: adenine, guanine, cytosine, thymine, uracil, or a group which does not inhibit complementary base pairing of an adjacent base to a complementary nucleic acid; and provided that the molecule contains about 5 to about 35 bases independently selected from the group consisting of: adenine, guanine, cytosine, thymine, and uracil. The terminal portion of the molecule contains $R_1$ and $R_2$ independently selected from the group consisting of OH, $C_1$–$C_6$ alkyl, and phosphate.

Peptide nucleic acid in a DNA analogue where the deoxyribose phosphate backbone is replaced by a pseudo peptide backbone. Peptide nucleic acid is described by Hyrup and Nielsen, Bioorganic & Medicinal Chemistry 4:5–23, 1996, and Hydig-Hielsen and Godskesen, International Application Number PCT/DK95/00195, International Publication WO 95/32305, each of which is hereby incorporated by reference herein.

Preferably, the peptide nucleic acid is made up of N-(2-aminoethyl)glycine units as illustrated in Structure II.

STRUCTURE II

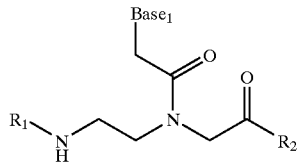

Where $R_1$, $R_2$, and Base$_1$ are as described for Structure I type molecules.

Nucleotide base recognition sequences can be produced using standard techniques. Publications describing organic synthesis of oligonucleotides and modified oligonucleotides include Eckstein, F., Oligonucleotides and Analogues, A Practical Approach, chapters 1–5, 1991, that reviews organic synthesis of oligonucleotides; Caruthers et al., Methods In Enzymology vol. 154 p. 287 (1987), that describes a procedure for organic synthesis of oligonucleotides using standard phosphoramidite solid-phase chemistry; Bhatt, U.S. Pat. No. 5,252,723, that describes a procedure for organic synthesis of modified oligonucleotides containing phosphorothioate linkages; and Klem et al., WO 92/07864, that describes organic synthesis of modified oligonucleotides having different linkages including methylphosphonate linkages. (Each of these references is hereby incorporated by reference herein.)

Additional references describing techniques that can be used to produce different types of nucleotide base recognition sequences include Cook, International Application No.

PCT/US92/11339, International Publication WO 93/13121; Miller et al., International Application No. PCT/US94/00157, International Publication WO 94/15619; McGee et al., International Application No. PCT/US93/06807, International Publication WO 94/02051; Cook et al., International Application No. PCT/US93/01579, International Publication WO 94/19023; Hyrup and Nielsen, Bioorganic & Medicinal Chemistry 4:5–23, 1996; and Hydig-Hielsen and Godskesen, International Application Number PCT/DK95/00195, International Publication WO 95/32305. (Each of these references is hereby incorporated by reference herein.)

Labels can be attached to a molecular torch by various means including covalent linkages, chelation, and ionic interactions. Preferably, a label is covalently attached.

Molecular torches present during an amplification protocol preferably do not contain a terminal 3' OH available for primer extension. Blocking groups that can inhibit primer extension by a nucleic acid polymerase may be located at or near the 3' end of a nucleic acid molecular torch. "At or near" the 3' end refers to a blocking group present within five bases of the 3' terminus. If a blocking group is not placed at the 3' terminus of a nucleic acid molecular torch, it should be sufficiently large so as to effect binding of a DNA polymerase to the torch.

Preferably, a nucleic acid molecular torch contains a blocking group located at its 3' terminus. By attaching a blocking group to a terminal 3' OH, the 3' OH group is no longer available to accept a nucleoside triphosphate in a polymerization reaction.

Numerous different chemical groups can be used to block the 3' end of a nucleic acid sequence. Examples of such groups include alkyl groups, non-nucleotide linkers, alkanediol dideoxynucleotide residues, and cordycepin.

The target binding region should be long enough to bind specifically to a desired target. A bacterial target binding region is preferably at least about 10 recognition groups, more preferably at least 12 recognition groups. A complex target binding region for a multi-cell organism such as a human, is preferably at least about 16 recognition groups, more preferably at least 18 recognition groups.

In an embodiment of the present invention concerned with the target binding domain, the target binding domain is made up of about 7 to about 40 recognition groups, and 0 to about 4 non-nucleotide monomeric groups each opposite a recognition group in the target closing domain. In preferred embodiments, at least about 8, more preferably at least about 10 recognition groups are present; no more than about 30, no more than about 25, and no more than about 15 recognition groups are present; and no more than 2, preferably no more than 1, and most preferably 0 non-nucleotide monomeric groups are present. Preferably, each non-nucleotide monomeric group is an abasic "nucleotide".

A non-nucleotide monomeric group provides a distance between adjunct groups containing nucleotide bases which is about the same length as in a nucleic acid. Thus, a non-nucleotide monomeric group joining two nucleotides positions the nucleotides so that they can hydrogen bond to complementary nucleotides in a nucleic acid.

In an embodiment of the present invention concerned with the target closing domain, the target closing domain is made up of about 7 to about 40 recognition groups, and 0 to about 6 non-nucleotide monomeric groups or mismatches with the target binding domain. In different embodiments, at least about 8, or at least about 10 recognition groups are present; no more than about 30, no more than about 25, and no more than about 15 recognition groups are present; and 0, 1, 2, 3, 4, 5 or 6 non-nucleotide monomeric groups or mismatches with the target binding domain are present. Preferably, each non-nucleotide monomeric group is an abasic "nucleotide". More preferably, mismatches rather than abasic nucleotides are present.

Preferably, the target binding domain is substantially comprised of independently selected 2'-methoxy or 2'-fluoro substituted ribonucleotides, and the target closing domain is substantially comprised of independently selected deoxyribonucleotides. "Substantially comprised" or "substantially comprises" indicates that the referenced component(s) makes up at least 70%, at least 80%, at least 90%, or 100% of the target opening domain or target closing domain.

The joining region can be produced using techniques well known in the art taking into account the composition of the joining region. Preferably, the joining region contains different members of a binding set able to bind together, where the target binding domain is joined to one member of the binding set and the target closing domain is joined to another member of the binding set. A member of a binding set can bind to another member of the same binding set. Examples of binding sets include substantially complementary nucleotide base recognition sequences, antibody/antigen, enzyme/substrate, and biotin/avidin.

Members of a binding set positioned adjacent or near to the target opening and target closing domains can effect the stability of a target binding domain:target closing domain hybrid. Too large an effect can make it difficult to produce an open torch because the target binding domain:target closing domain hybrid may remain intact under a wide range of conditions. The affect of a binding set on the stability of a target binding domain:target closing domain hybrid can be determined, for example, by measuring the $T_m$ of the hybrid.

Members of binding sets can be covalently linked together using one or more linkers. Examples of linkers include optionally substituted alkyl groups, polynucleotides and non-nucleotide linkers. Non-nucleotide linkers include polysaccharides, polypeptides, and abasic "nucleotides".

Polynucleotides used as linker groups between the target opening and target closing domains are preferably designed not to hybridize to the target sequence, or other nucleic acids which may be present in the sample. Though some binding to the target may be advantageous, for example, when strand displacement conditions are used. Preferred polynucleotide linker groups are poly T, poly A, and mixed poly A-T. Polynucleotide linker groups are preferably 5 to 25 nucleotides.

Molecular torches can include single-stranded regions complementary to the target sequence that, for example, may be positioned next to the target binding domain and may be part of the joining region. Preferably, such single-stranded regions contain no more than about ten nucleotide base recognition groups complementary to the target sequence. More preferably, such single-stranded regions, if present, are no more than ten, five, three, two, or one nucleotide base recognition groups complementary to the target sequence.

Linker groups can be positioned between binding set members and the target opening and target closing domains to decrease the effect of binding set members on the target binding domain:target closing domain hybrid. The placement of linker groups between, for example, a binding set member and the target binding domain physically separates the binding set member from the target binding domain thereby decreasing the affect of the binding set member on the target binding domain:target closing domain hybrid.

Additional examples are provided below illustrating different aspects and embodiments of the present invention.

These examples are not intended in any way to limit the disclosed invention.

EXAMPLE 1

Tuning of the Target Binding Domain:Target Closing Domain $T_m$

This example illustrates the use of different molecular torch design factors to obtain a desired target binding domain:target closing domain hybrid $T_m$. The $T_m$ of four different molecular torches was adjusted in this example using non-nucleotide, polyethylene glycol (PEG) linkers, a combination of mismatched bases, abasic "nucleotides" (i.e., bulges), and 2'-methoxy substituted ribonucleotides.

The different molecular torches used in this example were constructed from four different strands, as shown in FIGS. 6A and 6B. In these figures, "F" refers to an EDANS fluorophore, "Q" refers to a DABCYL quencher, and the "ccc" group at the 3'-end of one strand of each torch refers to a three carbon group which functions as a primer extension blocking group. The nucleotides of these molecular torches are either deoxyribonucleotides or 2'-methoxy substituted ribonucleotides (indicated with bold/italics). All of the molecular torches used in this example contain a joining region composed of a non-nucleotide, 20 Å PEG group and a double-stranded, 2'-methoxy substituted ribonucleotide duplex that alone exhibits a very high $T_m$ (>90° C.).

As shown in FIG. 6B, Torch 1 is made up of Strands 2 and 3; Torch 2 is made up of Strands 2 and 4; Torch 3 is made up of Strands 1 and 3; and Torch 4 is made up of Strands 1 and 4. Each of Strands 1–4 (shown in FIG. 6A) includes two nucleotide base recognition sequences separated by a PEG group, where Strand 1 included the nucleotide base recognition sequences of SEQ ID NO: 1 (5'-cagugcaggn ggaaag-3') and SEQ ID NO: 2 (5'-ggcuggacug cgugcg-3'); Strand 2 included the nucleotide base recognition sequences SEQ ID NO: 2 and SEQ ID NO: 3 (5'-cagugcaggg gaaag-3'); Strand 3 included the nucleotide base recognition sequences of SEQ ID NO: 4 (5'-cttttccttg ctctg-3') and SEQ ID NO: 5 (5'-cgcacgcagu ccagcc-3'); and Strand 4 included the nucleotide base recognition sequences of SEQ ID NO: 5 and SEQ ID NO: 6 (5'-ctttnncccc tgcnnactg-3').

In all four molecular torches, the target binding domain was made up of 2'-methoxy substituted ribonucleotides and the target closing domain was made up of deoxyribonucleotides. The underlined groups indicate mismatches while "n" denotes abasic bulges.

The stability of different hybrids was determined using a mixture containing 500 pmol of each strand added to 350 μl of KEMPS buffer. (KEMPS is made up of 100 mM KCl, 0.1 mM EDTA, 10 mM MgCl$_2$, 50 mM PIPES (pH 6.85), and 1 mM spermine.) The mixture was heated to 80° C. for 15 minutes and then subjected to $T_m$ analysis. $T_m$ was measured optically at 260 nm over a range of 45–95° C. at 0.5° C. min$^{-1}$ using a Beckman DU-640 melting apparatus.

Table 1 summarizes the stability of the target binding domain:target closing domain hybrid in the four molecular torches tested. Table 1 also highlights some of the design factors affecting hybrid stability.

TABLE 1

| Torch | Melting Temperature (° C.) | Factors Affecting Hybrid Stability |
| --- | --- | --- |
| 1 | 76.9 | Three mismatched base pairs |
| 2 | 89.4 | Two sets of 2 abasic bulges ("n") in a deoxy strand |

TABLE 1-continued

| Torch | Melting Temperature (° C.) | Factors Affecting Hybrid Stability |
| --- | --- | --- |
| 3 | 64.5 | 1 abasic bulge ("n") in a methoxy strand, plus 3 mismatched base pairs |
| 4 | 72.9 | 1 abasic bulge ("n") in methoxy, two sets of 2 abasic bulges ("n") in a deoxy strand |

Note: "deoxy" refers to deoxyribonucleotides and "methoxy" refers to 2'-methoxy substituted ribonucleotides.

As illustrated in Table 1, the $T_m$ of a molecular torch can be tuned using different factors affecting hybrid stability. Other factors affecting hybrid stability, such as those described herein and those well known in the art, can also be used to obtain a desired hybrid $T_m$ in different solutions.

EXAMPLE 2

Molecular Torch Binding to a Target Sequence

Torch 5, as shown in FIG. 6B, is the same as Torch 1, except that the PEG linker of strands 2 and 3 was replaced with the deoxyribonucleotide sequences of 5'-tttcttttcttt-3' and 5'-ttttcttctttc-3', respectively, so that the nucleotide base recognition sequences of Torch 5 were SEQ ID NO: 7 (5'-cagugcaggg gaaagtttct tttctttggc uggacugcgu gcg-3') and SEQ ID NO: 8 (5'-cgcacgcagu ccagcctttt cttctttcct tttccttgct ctg-3'). Torch 5 also contained an EDANS fluorophore ("F") and a DABCYL quencher ("Q"), which were used to detect the presence of a synthetic RNA target sequence. Torch 5 had a target binding domain (SEQ ID NO: 3) made up of 2'-methoxy substituted ribonucleotides (indicated with bold/italics), and a target closing domain (SEQ ID NO: 4) made up of deoxyribonucleotides. The target binding domain was perfectly complementary to the target sequence but had three mismatches to the target closing domain.

Torch 5 was generated by first producing a mixture containing the EDANS and DABCYL strands in KEMPS buffer (as described in Example 1 supra) at pH 6.85. The mixture was heated to 60° C. for 10 minutes and then cooled to room temperature.

Approximately 80 pmol of Torch 5 were incubated with increasing amounts of the RNA target molecule. The sample was heated to 60° C. for 20 minutes to open torches and allow for hybridization between the target binding domain and the target sequence, and then cooled to room temperature to close torches which had not hybridized to the target sequence. The control sample contained 90 mM of target and was not heated to 60° C. (the sample was maintained at room temperature).

Fluorescence was measured using a Spex Fluorolog-2 spectrophotometer (ISA Jobin Yvon-Spex; Edison, N.J.). The emission wavelength was 495 nm, and the excitation wavelength was 360 nm. Table 2 summarizes the results of the experiment.

TABLE 2

| Incubation Temperature (° C.) | RNA Target Level (pmol) | Fluorescence Data @ 495 nm (cps) |
| --- | --- | --- |
| 60 | 0 | 11,800 |
| 60 | 30 | 54,000 |
| 60 | 60 | 89,000 |
| 60 | 90 | 94,000 |
| Room | 90 | 17,300 |

The results show that this molecular torch binds approximately stoichiometrically to the target sequence. And, under the conditions employed, the target binding domain is unavailable for binding to the target sequence in the absence of heat, thus producing little signal even in the presence of the target sequence.

EXAMPLE 3
Effect of Different Environments

This example illustrates the use and affect of different solution environments and different torch constructs. The different solutions used in this example contain different components for transcription-associated amplification reactions.

Torches 1, 6 and 7 (Torches 1 and 6 are shown in FIG. 6, while Torch 7 is not shown) were used in this example. Torch 1 is described in Example 1 supra, while Torch 6 contained a 20 Å PEG joining region which joined a 2'-methoxy substituted ribonucleotide target binding domain (SEQ ID NO: 3) (indicated with bold/italics) and a deoxyribonucleotide target closing domain (SEQ ID NO: 4). Torch 6 also included a fluorescein fluorophore ("F") and a DABCYL quencher ("Q"). Torch 7 was a Torch 6 analog, where the target closing domain (SEQ ID NO: 4) was made up of modified nucleotides having the phosphodiester linkages replaced with phosphorothioate linkages.

A specified amount of a synthetic RNA target sequence, if any, and 25 pmol of molecular torch were mixed together in 100 μl of the solution which was used in creating Conditions A, B, C and D described below. After creating conditions A, B, C and D, each solution was heated to 65° C. for 20 minutes, and then cooled to room temperature for 10 minutes.

Conditions A, B, C and D included reagents selected from the following groups of reagents:

Reagent 1: 40 mM trehalose, 4 mM HEPES, 25 mM NaIc, 0.02 mM EDTA, 0.04% Triton® X-102, and 0.02 mM zinc acetate, at pH 7.0;

Reagent 2: 12.5 mM $MgCl_2$, 17.5 mM KCl, 0.15 mM zinc acetate, 5% glycerol, 6.25 mM ATP, 2.5 mM CTP, 6.25 mM GTP, 2.5 mM UTP, 0.2 mM dATP, 0.2 mM dCTP, 0.2 mM dGTP, 0.2 mM dTTP, 50 mM Trizma base, 53 mM trehalose, 100 μM desferoxamine, and 2 mM spermidine, at pH 8.0;

Reagent 3: 18 mM KCl, 4% glycerol, 4 mM HEPES, 0.1 mM EDTA, and 0.0002% phenol red, at pH 7.0; and Reagent 4: 40 mM trehalose, 4 mM HEPES, 25 mM NaIc, 0.02 mM EDTA, 0.04% Triton® X-102, 0.02 mM zinc acetate, 18 mM KCl, 4% glycerol, 4 mM HEPES, 0.1 mM EDTA, and 0.0002% phenol red, at pH 7.0.

Condition A was made up of 25 μl of Reagent 2, 20 μl of Reagent 4, 50 μl of sample, reverse transcriptase (~33.4 μg), T7 RNA polymerase (~540 ng) and primers. Condition B was made up of 20 μl Reagent 3, 25 μl of Reagent 2, 50 μl of sample, and primers. Condition C was the same as condition A, but without the presence of primers. Condition D was the same as condition B, but without the presence of primers.

Fluorescence was measured using a Spex MicroMax microtiter plate reader and a Fluorolog-2 spectrophotometer using a band pass filter (485 nm) on the excitation momochrometer. Fluorescence was measured using an excitation wavelength of 491 nm and an emission wavelength of 522 nm. The results are shown in Table 3.

TABLE 3

| Condition | RNA Target Level (pmol) | Fluorescence Data @ 522 nm (cps) | | |
|---|---|---|---|---|
| | | Torch 1 | Torch 7 | Torch 6 |
| A | 0 (No Torch) | 14,000 | 17,000 | 13,000 |
| | 0 | 13,000 | 18,000 | 12,100 |
| | 5 | 35,000 | 25,400 | 30,000 |
| | 40 | 68,000 | 35,100 | 56,500 |
| B | 0 (No Torch) | 27,000 | 74,000 | 27,000 |
| | 0 | 30,000 | 70,000 | 29,300 |
| | 5 | 50,500 | 78,100 | 46,700 |
| | 40 | 65,000 | 94,500 | 67,500 |
| C | 0 (No Torch) | 16,000 | 18,000 | 14,000 |
| | 0 | 10,000 | 18,000 | 13,600 |
| | 5 | 39,000 | 24,100 | 28,000 |
| | 40 | 69,000 | 39,000 | 54,000 |
| D | 0 (No Torch) | 30,000 | 82,000 | 31,000 |
| | 0 | 31,000 | 62,000 | 35,300 |
| | 5 | 54,000 | 87,100 | 48,700 |
| | 40 | 76,000 | 106,500 | 70,500 |

For each of the different molecular torches examined in the different environments, an increase in signal was observed as the amount of target sequence increased. The amount of background signal varied depending upon the torch composition and the environment.

EXAMPLE 4
Detecting Amplified RNA Transcripts

This example illustrates the use of molecular torches present during a transcription-associated amplification procedure (discussed supra) to detect the production of target RNA transcripts. Transcription-associated amplification was performed in the presence of molecular torches and, following amplification, the presence of RNA transcripts was determined with either Torch 6 or a single-stranded, acridinium ester-labeled polynucleotide probe.

For this example, eight separate transcription replicates were generated in the presence of 20 pmol of Torch 6 and employing conditions specified as Condition A in Example 3 supra (except that 1 mM of each dNTP was employed instead of the 0.2 mM indicated for Reagent 2) at each of five different RNA target sequence levels (i.e., 0, 100, 500, 1000 and 5000 copies of the target RNA sequence), and for each target sequence level, the eight replicates were pooled into two separate groups of four replicates each. The amplification was carried out at 42° C. Following amplification, 350 μl of each pooled reaction solution was heated to 60° C. for 20 minutes to open the molecular torch, thereby permitting hybridization of the target binding domain (SEQ ID NO: 3) to the target transcript. The sample was then cooled to room temperature so that torches which were not hybridized to target would close.

Torch 6 binding to the target sequence was measured using a Spex MicroMax microtiter plate reader and Spex Fluorolog-2 spectrophotometer. Fluorescence was measured using an excitation wavelength of 491 nm and an emission wavelength of 522 nm.

Acridinium ester-labeled probes perfectly complementary to the target sequence were used as a control to determine the extent of amplification. The acridinium ester-labeled probes were employed using a homogeneous protection assay ("HPA") format.

HPA was carried out on 50 μl of each pooled reaction solution using a probe mix containing about 3,000,000 total RLUs of acridinium ester-labeled probe and 400 pmol of cold probe.

HPA formats using acridinium ester-labeled probe to detect target sequence are described in different references such as Arnold et al., U.S. Pat. No. 5,283,174, Nelson et al., "Detection Of Acridinium Esters By Chemiluminescence" in: Nonisotopic DNA Probe Techniques, (Kricka ed., Academic Press, 1992) pp. 275–311, and Nelson et al., Clin. Chem. Acta 194:73–90, 1990, each of which is hereby incorporated by reference herein.

TABLE 4

Experiment 1

| Target Copy Number (Starting) | HPA Data (RLUs) | Fluorescence Data @ 522 nm (cps) |
|---|---|---|
| 0 | 7,096 | 869,000 |
| 100 | 8,711 | 872,000 |
|  | 9,109 | 870,000 |
| 500 | 29,092 | 1,377,000 |
|  | 20,910 | 1,043,000 |
| 1000 | 22,262 | 1,143,000 |
|  | 7,612 | 860,000 |
| 5000 | 89,389 | 1,623,000 |
|  | 73,971 | 1,670,000 |

TABLE 5

Experiment 2

| Target Copy Number (Starting) | HPA Data (RLUs) | Fluorescence Data @ 522 nm (cps) |
|---|---|---|
| 0 | 2,879 | 919,000 |
|  | 4,515 | 1,080,000 |
| 100 | 11,789 | 1,222,000 |
|  | 9,404 | 1,159,000 |
| 500 | 14,221 | 1,379,000 |
|  | 14,641 | 1,351,000 |
| 1000 | 19,931 | 1,697,000 |
|  | 24,052 | 1,607,000 |
| 5000 | 134,126 | 3,465,000 |
|  | 3,378 | 1,045,000 |

In both of these experiments there was an overall linear relationship between the amount of target RNA transcript detected by HPA using an acridinium ester-labeled probe and the amount of target RNA transcripts detected by the molecular torch. In Experiment 1, the sensitivity of the assay was 500 copies of target sequence. In Experiment 2, RNA transcripts were detected above background from amplification reactions starting with 100 copies of target sequence.

EXAMPLE 5

Strand Displacement of Molecular Torch by Target Sequence

Figure 7:
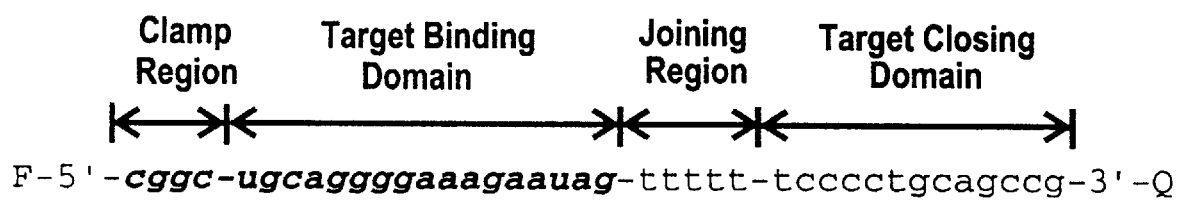
FIG. 7 illustrates a molecular torch which can be used in a strand displacement reaction. "F" refers to fluorophore and "Q" refers to quencher.
Figure 8:
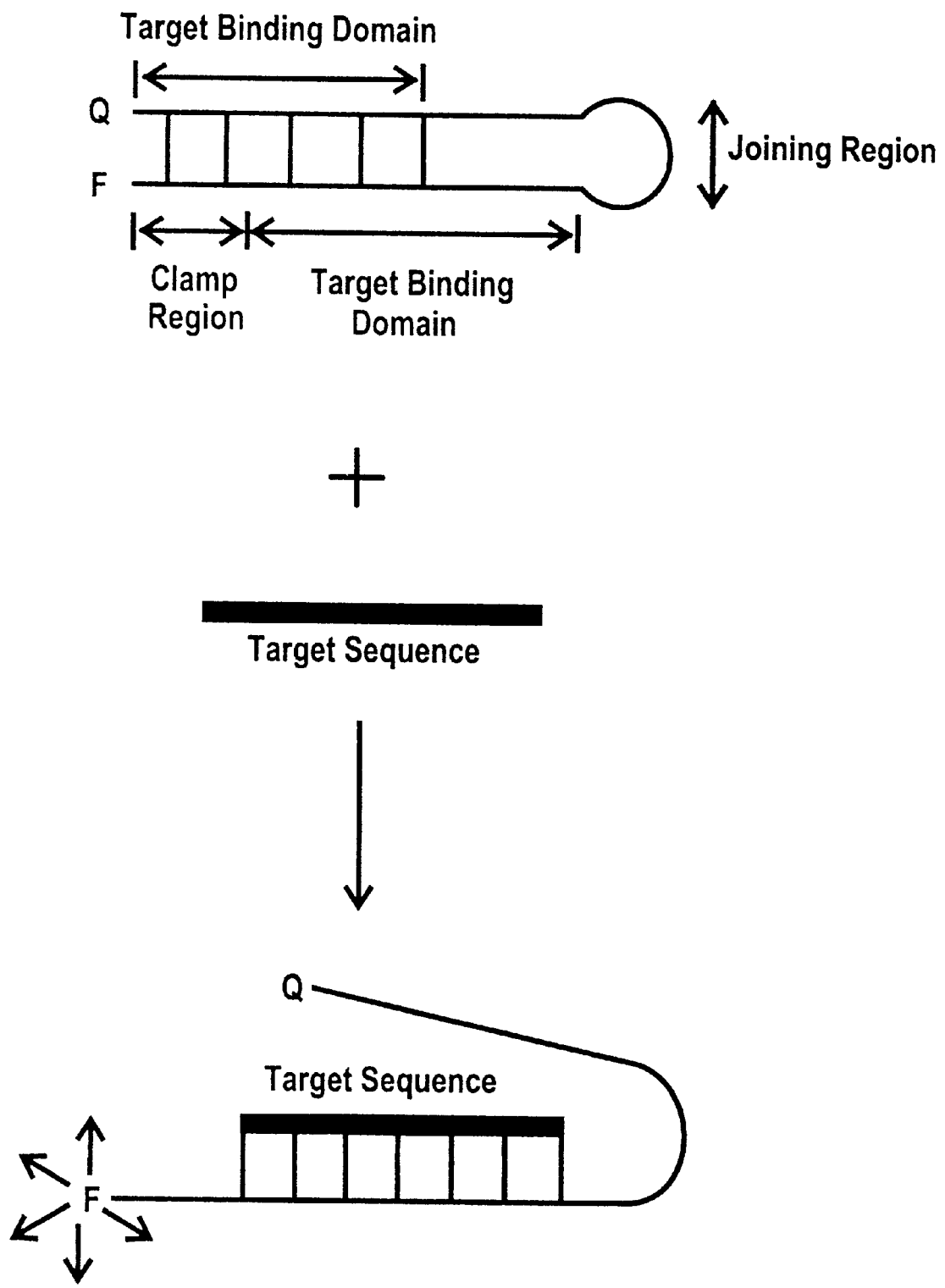
FIG. 8 illustrates the functioning of a molecular torch in a strand displacement reaction. "F" refers to fluorphore and "Q" refers to quencher. Target sequence is shown by a bolded line.

This example demonstrates that molecular torches can be designed to bind and detect target sequences under essentially constant environmental conditions. For this experiment, Torch 8 (see FIG. 7) was designed and tested for its ability to detect an RNA target sequence in solution. Torch 8 was made up of the nucleotide base recognition of SEQ ID NO: 9 (5'-cggcugcagg ggaaagaaua gtttttccc ctgcagccg-3'), where the 5'-ugcagggaaagaauag-3' portion represents the target binding domain, the 5'-tcccctgcagccg-3' portion represents the target closing domain, the 5'-cggc-3' portion represents a "clamp" region for binding a portion of the target closing domain sequence, and the 5'-ttttt-3' portion was a deoxyribonucleotide joining region. A portion of the target binding domain (5'-aagaauag-3') remained unbound to facilitate strand displacement of the target closing domain by the target. The target binding domain was fully complementary to the target sequence and both the target binding domain and the clamp region were made up of 2'-methoxy substituted ribonucleotides (indicated with bold/italics). The target closing domain was made up of deoxyribonucleotides. Torch 8 also included a fluorescein fluorophore ("F") and a DABCYL quencher ("Q").

In this experiment, 100 μl of Krammer buffer (20 mM TrisCl at pH 8.0, 5 mM MgCl, and 0.2% Tween®-20) was added to each of 10 microtiter wells of a white Cliniplate (Labsystems, Inc.; Franklin, Mass.). Increasing concentrations of the target sequence were added to the 10 buffer-containing wells in increasing amounts as indicated in Table 6 below, followed by the addition of 30 pmol of Torch 8 to each of the 10 wells. The plate was then manually agitated for 10–15 seconds before covering the fluid surface of each well with 50 μl of oil, which was used to limit evaporation and contamination. The plate was maintained at room temperature for a period of 10 minutes to permit target sequence sufficient time to displace the target closing domain and bind the target binding domain. Fluorescence signals from each well were then measured using a Spex MicroMax plate reader and a Spex Fluorolog-2 spectrophotometer, with an emission wavelength of 495 nm and an excitation wavelength of 525 nm. Table 6 provides the results of this experiment.

TABLE 6

| RNA Target Level (pmol) | Fluorescence Data @ 525 nm (cps) |
|---|---|
| 0 (No Torch) | 4,728 |
| 0 | 58,460 |
| 2.5 | 99,220 |
| 5 | 149,200 |
| 10 | 290,786 |
| 20 | 576,624 |
| 40 | 875,120 |
| 50 | 938,640 |
| 100 | 1,117,912 |
| 250 | 1,190,892 |

The results of this experiment show that the target sequence was able to strand invade Torch 8 and bind with the target binding domain at room temperature. In addition, the results show that the amount of target sequence which bound torch in the wells increased with the amount of target sequence present in a well, indicating that the torches of this invention may also be useful for quantifying the amount of target which may be present in a sample.

Other embodiments are within the following claims. Thus, while several embodiments have been shown and described, various modifications may be made without departing from the spirit and scope of the present invention.

What is claimed is:

1. A method for determining the presence of a target nucleic acid sequence in a sample, said method comprising the steps of:
   a) contacting said sample with a molecular torch comprising:
      a target binding domain comprising nucleotide base recognition groups;
      a target closing domain comprising nucleotide base recognition groups, wherein said target binding domain is biased toward said target sequence, such that said target binding domain forms a more stable hybrid with said target sequence than with said target closing domain under strand displacement conditions; and
      a joining region which joins said target binding domain and said target closing domain, wherein said joining region is selected from the group consisting of:
      one or more non-nucleotide linkers;
      first and second polynucleotides, or derivatives thereof, said first and second polynucleotides, or derivatives thereof, being substantially complementary to each other; and
      a combination of said one or more non-nucleotide linkers and said first and second polynucleotides or derivatives thereof,
      wherein said joining region facilitates the formation of a target binding domain:target closing domain hybrid in the absence of said target sequence;
   b) exposing said sample to strand displacement conditions; and
   c) determining whether a target binding domain:target sequence hybrid is present in said sample as an indication of the presence or absence of said target sequence in said sample.

2. The method of claim 1, wherein said target binding domain comprises 7 to about 40 of said nucleotide base recognition groups and 0 to about 4 non-nucleotide monomeric groups, each said non-nucleotide monomeric group being opposite one of said nucleotide base recognition groups present in said target closing domain.

3. The method of claim 2, wherein each said non-nucleotide monomeric group is an abasic nucleotide.

4. The method of claim 1, wherein said target closing domain comprises 7 to about 40 of said nucleotide base recognition groups and 0 to about 6 non-nucleotide monomeric groups or mismatches with said target binding domain.

5. The method of claim 4, wherein each said non-nucleotide monomeric group is an abasic nucleotide.

6. The method of claim 1, wherein at least 70% of said nucleotide base recognition groups of said target binding domain bind to said nucleotide base recognition groups of said target closing domain under said strand displacement conditions.

7. The method of claim 1, wherein at least 80% of said nucleotide base recognition groups of said target binding domain bind to said nucleotide base recognition groups of said target closing domain under said strand displacement conditions.

8. The method of claim 1, wherein at least 90% of said nucleotide base recognition groups of said target binding domain bind to said nucleotide base recognition groups of said target closing domain under said strand displacement conditions.

9. The method of claim 1, wherein said target binding domain includes from 1 to about 10 of said nucleotide base recognition groups which are accessible to said target sequence under said strand displacement conditions.

10. The method of claim 9, wherein up to 5 of said nucleotide base recognition groups of said target binding domain are accessible to said target sequence under said strand displacement conditions.

11. The method of claim 9, wherein up to 3 of said nucleotide base recognition groups of said target binding domain are accessible to said target sequence under said strand displacement conditions.

12. The method of claim 1, wherein the 5' end or the 3' end of said target binding domain includes from 1 to about 10 of said nucleotide base recognition groups which are accessible to said target sequence under said strand displacement conditions.

13. The method of claim 1, wherein said target binding domain:target closing domain hybrid includes from 1 to about 10 nucleotide base recognition groups which are accessible to said target sequence under said strand displacement conditions.

14. The method of claim 1, wherein:
said target sequence is RNA;
said target binding domain is substantially comprised of nucleotide base recognition groups which more stably bind to ribonucleotides than to deoxyribonucleotides; and
said target closing domain is substantially comprised of deoxyribonucleotides.

15. The method of claim 14, wherein said target binding domain substantially comprises 2'-methoxy or 2'-fluoro substituted ribonucleotides.

16. The method of claim 1, wherein each of said first and second polynucleotides substantially comprises nucleotide base recognition groups which more stably bind to ribonucleotides than to deoxyribonucleotides.

17. The method of claim 16, wherein said first and second polynucleotides comprise 2'-methoxy or 2'-fluoro substituted ribonucleotides.

18. The method of claim 1, wherein said joining region consists of said one or more non-nucleotide linkers.

19. The method of claim 18, wherein at least one of said non-nucleotide linkers is a polysaccharide or a polypeptide.

20. The method of claim 1, wherein said joining region consists of said first and second polynucleotides or derivatives thereof.

21. The method of claim 1, wherein said joining region consists of two of said non-nucleotide linkers and said first and second polynucleotides or derivatives thereof.

22. The method of claim 1, wherein:
said target binding domain or said target closing domain comprises a label; and
said label produces a first signal when said target binding domain:target closing domain hybrid is formed and a second signal when said target binding domain:target closing domain hybrid is not formed, said first and second signals being distinguishable.

23. The method of claim 1, wherein:
said target binding domain comprises a first label and said target closing domain comprises a second label;
said first and second labels interact to produce a first signal when said target binding domain and said target closing domain form a target binding domain:target closing domain hybrid and a second signal when said target binding domain and said target closing domain do not form said target binding domain:target closing domain hybrid, said first and second signals being distinguishable; and
an interaction change between said first and second labels is detected in step c) as an indication of the presence of a target binding domain:target sequence hybrid.

24. The method of claim 23, wherein said first label is attached to the end of said target binding domain which is not joined to said joining region and said second label is attached to the end of said target closing domain which is not joined to said joining region.

25. The method of claim 23, wherein said first and second labels comprise a luminescent/quencher pair.

26. The method of claim 23, wherein said first and second labels comprise a fluorophore/quencher pair.

27. The method of claim 23, wherein said first and second labels comprise a luminescent/adduct pair.

28. The method of claim 23, wherein said first and second labels comprise a Förrester energy transfer pair.

29. The method of claim 23, wherein said first and second labels comprise a dye dimer pair.

30. The method of claim 1, wherein said molecular torch further comprises a blocking group which can inhibit primer extension by a nucleic acid polymerase.

31. The method of claim 30, wherein said blocking group is located at or near a 3' end of said molecular torch.

32. The method of claim 31, wherein said blocking group is selected from the group consisting of an alkyl group, a non-nucleotide linker, an alkane-diol dideoxynucleotide residue and cordycepin.

33. The method of claim 1, wherein said strand displacement conditions constitute essentially constant environmental conditions.

34. The method of claim 1 further comprising separating said molecular torch which has formed said target binding domain:target sequence hybrid from molecular torches present in said sample which have not formed a target binding domain:target sequence hybrid.

35. The method of claim 1, wherein said target sequence is the product of a transcription-associated amplification and said molecular torch is added to said sample prior to said amplification.

36. A molecular torch comprising:
a target binding domain comprising nucleotide base recognition groups;
a target closing domain comprising nucleotide base recognition groups, wherein said target binding domain is biased toward a target nucleic acid sequence, such that said target binding domain forms a more stable hybrid with said target sequence than with said target closing domain under strand displacement conditions; and a joining region which joins said target binding domain and said target closing domain, wherein said joining region is selected from the group consisting of:
one or more non-nucleotide linkers;
first and second polynucleotides, or derivatives thereof, said first and second polynucleotides, or derivatives thereof, being substantially complementary to each other; and
a combination of said one or more non-nucleotide linkers and said first and second polynucleotides or derivatives thereof,
wherein said joining region facilitates the hybridization of said target binding domain to said target closing domain.

37. The molecular torch of claim 36, wherein said target binding domain comprises 7 to about 40 of said nucleotide base recognition groups and 0 to about 4 non-nucleotide monomeric groups, each said non-nucleotide monomeric group being opposite one of said nucleotide base recognition groups present in said target closing domain.

38. The molecular torch of claim 37, wherein each said non-nucleotide monomeric group is an abasic nucleotide.

39. The molecular torch of claim 36, wherein said target closing domain comprises 7 to about 40 of said nucleotide base recognition groups and 0 to about 6 non-nucleotide monomeric groups or mismatches with said target binding domain.

40. The molecular torch of claim 39, wherein each said non-nucleotide monomeric group is an abasic nucleotide.

41. The molecular torch of claim 36, wherein at least 70% of said nucleotide base recognition groups of said target binding domain bind to said nucleotide base recognition groups of said target closing domain under strand displacement conditions.

42. The molecular torch of claim 36, wherein at least 80% of said nucleotide base recognition groups of said target binding domain bind to said nucleotide base recognition groups of said target closing domain under strand displacement conditions.

43. The molecular torch of claim 36, wherein at least 90% of said nucleotide base recognition groups of said target binding domain bind to said nucleotide base recognition groups of said target closing domain under strand displacement conditions.

44. The molecular torch of claim 36, wherein said target binding domain includes from 1 to about 10 of said nucleotide base recognition groups which are accessible to said target sequence under said strand displacement conditions.

45. The molecular torch of claim 44, wherein said target binding domain includes up to 5 of said nucleotide base recognition groups which are accessible to said target sequence under said strand displacement conditions.

46. The molecular torch of claim 44, wherein said target binding domain includes up to 3 of said nucleotide base recognition groups which are accessible to said target sequence under said strand displacement conditions.

47. The molecular torch of claim 36, wherein the 5' end or the 3' end of said target binding domain includes from 1 to about 10 of said nucleotide base recognition groups which are accessible to said target sequence under said strand displacement conditions.

48. The molecular torch of claim 36, wherein said target binding domain:target closing domain hybrid includes from 1 to about 10 of said nucleotide base recognition groups which are accessible to said target sequence under said strand displacement conditions.

49. The molecular torch of claim 36, wherein said target binding domain is substantially comprised of nucleotide base recognition groups which more stably bind to ribonucleotides than to deoxyribonucleotides, and wherein said target closing domain is substantially comprised of deoxyribonucleotides.

50. The molecular torch of claim 49, wherein said target binding domain comprises 2'-methoxy or 2'-fluoro substituted ribonucleotides.

51. The molecular torch of claim 36, wherein said joining region consists of said one or more non-nucleotide linkers.

52. The molecular torch of claim 51, wherein at least one of said non-nucleotide linkers is a polysaccharide or a polypeptide.

53. The molecular torch of claim 36, wherein said joining region consists of said first and second polynucleotides or derivatives thereof.

54. The molecular torch of claim 36, wherein said joining region consists of two of said non-nucleotide linkers and said first and second polynucleotides or derivatives thereof.

55. The molecular torch of claim 36, wherein said target binding domain or said target closing domain comprises a label, and wherein said label produces a first signal when said target binding domain:target closing domain hybrid is formed and a second signal when said target binding domain:target closing domain hybrid is not formed, said first and second signals being distinguishable.

56. The molecular torch of claim 36, wherein said target binding domain comprises a first label and said target closing domain comprises a second label, wherein said first and second labels interact to produce a first signal when said target binding domain and said target closing domain form a target binding domain:target closing domain hybrid and a second signal when said target binding domain and said target closing domain do not form said target binding domain:target closing domain hybrid, said first and second signals being distinguishable.

57. The molecular torch of claim 56, wherein said first label is attached to the end of said target binding domain which is not joined to said joining region and said second label is attached to the end of said target closing domain which is not joined to said joining region.

58. The molecular torch of claim 56, wherein said first and second labels comprise a luminescent/quencher pair.

59. The molecular torch of claim 56, wherein said first and second labels comprise a fluorophore/quencher pair.

60. The molecular torch of claim 56, wherein said first and second labels comprise a luminescent/adduct pair.

61. The molecular torch of claim 56, wherein said first and second labels comprise a Förrester energy transfer pair.

62. The molecular torch of claim 56, wherein said first and second labels comprise a dye dimer pair.

63. The molecular torch of claim 36, wherein said molecular torch further comprises a blocking group which can inhibit primer extension by a nucleic acid polymerase.

64. The molecular torch of claim 63, wherein said blocking group is located at or near a 3' end of said molecular torch.

65. The molecular torch of claim 63, wherein said blocking group is selected from the group consisting of an alkyl group, a non-nucleotide linker, an alkane-diol dideoxynucleotide residue and cordycepin.

* * * * *

SEQUENCE LISTING

<160> NUMBER OF SEQ ID NOS: 9

<210> SEQ ID NO 1
<211> LENGTH: 16
<212> TYPE: RNA
<213> ORGANISM: Artificial Sequence
<220> FEATURE:
<223> OTHER INFORMATION: Description of Artificial Sequence:
      nucleotide base recognition sequence
      substantially complementary to SEQ ID Nos. 4 and 6
<221> NAME/KEY: modified_base
<222> LOCATION: (1)
<223> OTHER INFORMATION: cm
<221> NAME/KEY: modified_base
<222> LOCATION: (2)
<223> OTHER INFORMATION: 2'-O-methyladenosine
<221> NAME/KEY: modified_base
<222> LOCATION: (3)
<223> OTHER INFORMATION: gm
<221> NAME/KEY: modified_base
<222> LOCATION: (4)
<223> OTHER INFORMATION: um
<221> NAME/KEY: modified_base
<222> LOCATION: (5)
<223> OTHER INFORMATION: gm
<221> NAME/KEY: modified_base
<222> LOCATION: (6)
<223> OTHER INFORMATION: cm
<221> NAME/KEY: modified_base
<222> LOCATION: (7)
<223> OTHER INFORMATION: 2'-O-methyladenosine
<221> NAME/KEY: modified_base
<222> LOCATION: (8)..(9)
<223> OTHER INFORMATION: gm
<221> NAME/KEY: modified_base
<222> LOCATION: (10)
<223> OTHER INFORMATION: abasic bulge
<221> NAME/KEY: modified_base
<222> LOCATION: (11)..(12)
<223> OTHER INFORMATION: gm
<221> NAME/KEY: modified_base
<222> LOCATION: (13)..(15)
<223> OTHER INFORMATION: 2'-O-methyladenosine
<221> NAME/KEY: modified_base
<222> LOCATION: (16)
<223> OTHER INFORMATION: gm

<400> SEQUENCE: 1
cngugcnggn ggnnng                                                16

<210> SEQ ID NO 2
<211> LENGTH: 16
<212> TYPE: RNA
<213> ORGANISM: Artificial Sequence
<220> FEATURE:
<223> OTHER INFORMATION: Description of Artificial Sequence:
      nucleotide base recognition sequence substantially
      complementary to SEQ ID NO: 5
<221> NAME/KEY: modified_base
<222> LOCATION: (1)..(2)
<223> OTHER INFORMATION: gm
<221> NAME/KEY: modified_base
<222> LOCATION: (3)
<223> OTHER INFORMATION: cm
<221> NAME/KEY: modified_base
<222> LOCATION: (4)
<223> OTHER INFORMATION: um
<221> NAME/KEY: modified_base
<222> LOCATION: (5)..(6)
<223> OTHER INFORMATION: gm
<221> NAME/KEY: modified_base
<222> LOCATION: (7)
<223> OTHER INFORMATION: 2'-O-methyladenosine
<221> NAME/KEY: modified_base

```
<222> LOCATION: (8)
<223> OTHER INFORMATION: cm
<221> NAME/KEY: modified_base
<222> LOCATION: (9)
<223> OTHER INFORMATION: um
<221> NAME/KEY: modified_base
<222> LOCATION: (10)
<223> OTHER INFORMATION: gm
<221> NAME/KEY: modified_base
<222> LOCATION: (11)
<223> OTHER INFORMATION: cm
<221> NAME/KEY: modified_base
<222> LOCATION: (12)
<223> OTHER INFORMATION: gm
<221> NAME/KEY: modified_base
<222> LOCATION: (13)
<223> OTHER INFORMATION: um
<221> NAME/KEY: modified_base
<222> LOCATION: (14)
<223> OTHER INFORMATION: gm
<221> NAME/KEY: modified_base
<222> LOCATION: (15)
<223> OTHER INFORMATION: cm
<221> NAME/KEY: modified_base
<222> LOCATION: (16)
<223> OTHER INFORMATION: gm

<400> SEQUENCE: 2
ggcuggncug cgugcg                                                  16

<210> SEQ ID NO 3
<211> LENGTH: 15
<212> TYPE: RNA
<213> ORGANISM: Artificial Sequence
<220> FEATURE:
<223> OTHER INFORMATION: Description of Artificial Sequence:
      nucleotide base recognition sequence substantially
      complementary to SEQ ID Nos. 4 and 6
<221> NAME/KEY: modified_base
<222> LOCATION: (1)
<223> OTHER INFORMATION: cm
<221> NAME/KEY: modified_base
<222> LOCATION: (2)
<223> OTHER INFORMATION: 2'-O-methyladenosine
<221> NAME/KEY: modified_base
<222> LOCATION: (3)
<223> OTHER INFORMATION: gm
<221> NAME/KEY: modified_base
<222> LOCATION: (4)
<223> OTHER INFORMATION: um
<221> NAME/KEY: modified_base
<222> LOCATION: (5)
<223> OTHER INFORMATION: gm
<221> NAME/KEY: modified_base
<222> LOCATION: (6)
<223> OTHER INFORMATION: cm
<221> NAME/KEY: modified_base
<222> LOCATION: (7)
<223> OTHER INFORMATION: 2'-O-methyladenosine
<221> NAME/KEY: modified_base
<222> LOCATION: (8)..(11)
<223> OTHER INFORMATION: gm
<221> NAME/KEY: modified_base
<222> LOCATION: (12)..(14)
<223> OTHER INFORMATION: 2'-O-methyladenosine
<221> NAME/KEY: modified_base
<222> LOCATION: (15)
<223> OTHER INFORMATION: gm

<400> SEQUENCE: 3
cngugcnggg gnnng                                                   15

<210> SEQ ID NO 4
<211> LENGTH: 15
<212> TYPE: DNA
```

```
<213> ORGANISM: Artificial Sequence
<220> FEATURE:
<223> OTHER INFORMATION: Description of Artificial Sequence:
      nucleotide base recognition sequence substantially
      complementary to SEQ ID Nos. 1 and 3

<400> SEQUENCE: 4
cttttccttg ctctg                                                          15

<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence:
      nucleotide base recognition sequence substantially
      complementary to SEQ ID NO: 2
<221> NAME/KEY: modified_base
<222> LOCATION: (1)
<223> OTHER INFORMATION: cm
<221> NAME/KEY: modified_base
<222> LOCATION: (2)
<223> OTHER INFORMATION: gm
<221> NAME/KEY: modified_base
<222> LOCATION: (3)
<223> OTHER INFORMATION: cm
<221> NAME/KEY: modified_base
<222> LOCATION: (4)
<223> OTHER INFORMATION: 2'-O-methyladenosine
<221> NAME/KEY: modified_base
<222> LOCATION: (5)
<223> OTHER INFORMATION: cm
<221> NAME/KEY: modified_base
<222> LOCATION: (6)
<223> OTHER INFORMATION: gm
<221> NAME/KEY: modified_base
<222> LOCATION: (7)
<223> OTHER INFORMATION: cm
<221> NAME/KEY: modified_base
<222> LOCATION: (8)
<223> OTHER INFORMATION: 2'-O-methyladenosine
<221> NAME/KEY: modified_base
<222> LOCATION: (9)
<223> OTHER INFORMATION: gm
<221> NAME/KEY: modified_base
<222> LOCATION: (10)
<223> OTHER INFORMATION: um
<221> NAME/KEY: modified_base
<222> LOCATION: (11)..(12)
<223> OTHER INFORMATION: cm
<221> NAME/KEY: modified_base
<222> LOCATION: (13)
<223> OTHER INFORMATION: 2'-O-methyladenosine
<221> NAME/KEY: modified_base
<222> LOCATION: (14)
<223> OTHER INFORMATION: gm
<221> NAME/KEY: modified_base
<222> LOCATION: (15)..(16)
<223> OTHER INFORMATION: cm

<400> SEQUENCE: 5
cgcncgcngu ccngcc                                                         16

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:
      nucleotide base recognition sequence
      substantially complementary to SEQ ID Nos. 1 and 3
<221> NAME/KEY: modified_base
<222> LOCATION: (5)..(6)
<223> OTHER INFORMATION: abasic bulge
<221> NAME/KEY: modified_base
```

```
<222> LOCATION: (14)..(15)
<223> OTHER INFORMATION: abasic bulge

<400> SEQUENCE: 6
ctttnncccc tgcnnactg                                                 19

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:
      nucleotide base recognition sequence substantially
      complementary to SEQ ID NO: 8, where residues 1-15
      and 28-43 are RNA and residues 16-27 are DNA
<221> NAME/KEY: modified_base
<222> LOCATION: (1)
<223> OTHER INFORMATION: cm
<221> NAME/KEY: modified_base
<222> LOCATION: (2)
<223> OTHER INFORMATION: 2'-O-methyladenosine
<221> NAME/KEY: modified_base
<222> LOCATION: (3)
<223> OTHER INFORMATION: gm
<221> NAME/KEY: modified_base
<222> LOCATION: (4)
<223> OTHER INFORMATION: um
<221> NAME/KEY: modified_base
<222> LOCATION: (5)
<223> OTHER INFORMATION: gm
<221> NAME/KEY: modified_base
<222> LOCATION: (6)
<223> OTHER INFORMATION: cm
<221> NAME/KEY: modified_base
<222> LOCATION: (7)
<223> OTHER INFORMATION: 2'-O-methyladenosine
<221> NAME/KEY: modified_base
<222> LOCATION: (8)..(11)
<223> OTHER INFORMATION: gm
<221> NAME/KEY: modified_base
<222> LOCATION: (12)..(14)
<223> OTHER INFORMATION: 2'-O-methyladenosine
<221> NAME/KEY: modified_base
<222> LOCATION: (15)
<223> OTHER INFORMATION: gm
<221> NAME/KEY: modified_base
<222> LOCATION: (28)..(29)
<223> OTHER INFORMATION: gm
<221> NAME/KEY: modified_base
<222> LOCATION: (30)
<223> OTHER INFORMATION: cm
<221> NAME/KEY: modified_base
<222> LOCATION: (31)
<223> OTHER INFORMATION: um
<221> NAME/KEY: modified_base
<222> LOCATION: (32)..(33)
<223> OTHER INFORMATION: gm
<221> NAME/KEY: modified_base
<222> LOCATION: (34)
<223> OTHER INFORMATION: 2'-O-methyladenosine
<221> NAME/KEY: modified_base
<222> LOCATION: (35)
<223> OTHER INFORMATION: cm
<221> NAME/KEY: modified_base
<222> LOCATION: (36)
<223> OTHER INFORMATION: um
<221> NAME/KEY: modified_base
<222> LOCATION: (37)
<223> OTHER INFORMATION: gm
<221> NAME/KEY: modified_base
<222> LOCATION: (38)
<223> OTHER INFORMATION: cm
<221> NAME/KEY: modified_base
<222> LOCATION: (39)
<223> OTHER INFORMATION: gm
<221> NAME/KEY: modified_base
<222> LOCATION: (40)
```

```
<223> OTHER INFORMATION: um
<221> NAME/KEY: modified_base
<222> LOCATION: (41)
<223> OTHER INFORMATION: gm
<221> NAME/KEY: modified_base
<222> LOCATION: (42)
<223> OTHER INFORMATION: cm
<221> NAME/KEY: modified_base
<222> LOCATION: (43)
<223> OTHER INFORMATION: gm

<400> SEQUENCE: 7
cngugcnggg gnnngtttct tttctttggc uggncugcgu gcg                43

<210> SEQ ID NO 8
<211> LENGTH: 43
<212> TYPE: DNA
<213> ORGANISM: Artificial Sequence
<220> FEATURE:
<223> OTHER INFORMATION: Description of Artificial Sequence:
      nucleotide base recognition sequence substantially
      complementary to SEQ ID NO: 7, where residues 1-16
      are RNA and residues 17-43 are DNA
<221> NAME/KEY: modified_base
<222> LOCATION: (1)
<223> OTHER INFORMATION: cm
<221> NAME/KEY: modified_base
<222> LOCATION: (2)
<223> OTHER INFORMATION: gm
<221> NAME/KEY: modified_base
<222> LOCATION: (3)
<223> OTHER INFORMATION: cm
<221> NAME/KEY: modified_base
<222> LOCATION: (4)
<223> OTHER INFORMATION: 2'-O-methyladenosine
<221> NAME/KEY: modified_base
<222> LOCATION: (5)
<223> OTHER INFORMATION: cm
<221> NAME/KEY: modified_base
<222> LOCATION: (6)
<223> OTHER INFORMATION: gm
<221> NAME/KEY: modified_base
<222> LOCATION: (7)
<223> OTHER INFORMATION: cm
<221> NAME/KEY: modified_base
<222> LOCATION: (8)
<223> OTHER INFORMATION: 2'-O-methyladenosine
<221> NAME/KEY: modified_base
<222> LOCATION: (9)
<223> OTHER INFORMATION: gm
<221> NAME/KEY: modified_base
<222> LOCATION: (10)
<223> OTHER INFORMATION: um
<221> NAME/KEY: modified_base
<222> LOCATION: (11)..(12)
<223> OTHER INFORMATION: cm
<221> NAME/KEY: modified_base
<222> LOCATION: (13)
<223> OTHER INFORMATION: 2'-O-methyladenosine
<221> NAME/KEY: modified_base
<222> LOCATION: (14)
<223> OTHER INFORMATION: gm
<221> NAME/KEY: modified_base
<222> LOCATION: (15)..(16)
<223> OTHER INFORMATION: cm

<400> SEQUENCE: 8
cgcncgcngu ccngcctttt cttctttcct tttccttgct ctg                43

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:
```

```
      nucleotide base recognition sequence, where
      residues 1-21 are RNA and residues 22-39 are DNA
<221> NAME/KEY: modified_base
<222> LOCATION: (1)
<223> OTHER INFORMATION: cm
<221> NAME/KEY: modified_base
<222> LOCATION: (2)..(3)
<223> OTHER INFORMATION: gm
<221> NAME/KEY: modified_base
<222> LOCATION: (4)
<223> OTHER INFORMATION: cm
<221> NAME/KEY: modified_base
<222> LOCATION: (5)
<223> OTHER INFORMATION: um
<221> NAME/KEY: modified_base
<222> LOCATION: (6)
<223> OTHER INFORMATION: gm
<221> NAME/KEY: modified_base
<222> LOCATION: (7)
<223> OTHER INFORMATION: cm
<221> NAME/KEY: modified_base
<222> LOCATION: (8)
<223> OTHER INFORMATION: 2'-O-methyladenosine
<221> NAME/KEY: modified_base
<222> LOCATION: (9)..(12)
<223> OTHER INFORMATION: gm
<221> NAME/KEY: modified_base
<222> LOCATION: (13)..(15)
<223> OTHER INFORMATION: 2'-O-methyladenosine
<221> NAME/KEY: modified_base
<222> LOCATION: (16)
<223> OTHER INFORMATION: gm
<221> NAME/KEY: modified_base
<222> LOCATION: (17)..(18)
<223> OTHER INFORMATION: 2'-O-methyladenosine
<221> NAME/KEY: modified_base
<222> LOCATION: (19)
<223> OTHER INFORMATION: um
<221> NAME/KEY: modified_base
<222> LOCATION: (20)
<223> OTHER INFORMATION: 2'-O-methyladenosine
<221> NAME/KEY: modified_base
<222> LOCATION: (21)
<223> OTHER INFORMATION: gm

<400> SEQUENCE: 9
cggcugcngg ggnnngnnun gttttttccc ctgcagccg                           39
```